(12) United States Patent
Burakowska-Meise et al.

(10) Patent No.: US 10,709,645 B2
(45) Date of Patent: Jul. 14, 2020

(54) MICROCAPSULES

(71) Applicant: BASF SE, Ludwigshafen (DE)

(72) Inventors: Ewelina Burakowska-Meise, Reichenbach (DE); Valeria Bem, Mannheim (DE); Roland Hinrich Staff, Guntersblum (DE); Brigitte Lindemann, Grenzach-Wyhlen (DE); Helmut Witteler, Wachenheim (DE)

(73) Assignees: BASF SE (DE); BASF Grenzach GmbH (DE)

( * ) Notice: Subject to any disclaimer, the term of this patent is extended or adjusted under 35 U.S.C. 154(b) by 0 days.

(21) Appl. No.: 15/532,900

(22) PCT Filed: Dec. 3, 2015

(86) PCT No.: PCT/EP2015/078554
§ 371 (c)(1),
(2) Date: Jun. 2, 2017

(87) PCT Pub. No.: WO2016/087598
PCT Pub. Date: Jun. 9, 2016

(65) Prior Publication Data
US 2017/0360660 A1   Dec. 21, 2017

(30) Foreign Application Priority Data
Dec. 4, 2014 (EP) ..................... 14196271

(51) Int. Cl.
| A61K 8/11 | (2006.01) |
| B01J 13/22 | (2006.01) |
| A61K 8/81 | (2006.01) |
| A61Q 17/04 | (2006.01) |
| B01J 13/08 | (2006.01) |

(52) U.S. Cl.
CPC ............ *A61K 8/11* (2013.01); *A61K 8/817* (2013.01); *A61K 8/8129* (2013.01); *A61Q 17/04* (2013.01); *B01J 13/08* (2013.01); *B01J 13/22* (2013.01); *A61K 2800/41* (2013.01); *A61K 2800/624* (2013.01); *A61K 2800/63* (2013.01)

(58) Field of Classification Search
None
See application file for complete search history.

(56) References Cited

U.S. PATENT DOCUMENTS

| 4,349,454 A * | 9/1982 | Iwasaki ................. B41M 5/136 264/4.7 |
| 6,951,836 B2 | 10/2005 | Jahns et al. |
| 2004/0247536 A1 | 12/2004 | Chaudhuri |
| 2007/0138671 A1 | 6/2007 | Anastasiou et al. |

FOREIGN PATENT DOCUMENTS

| DE | 1165574 B | 3/1964 |
| DE | 2024051 A1 | 12/1971 |
| DE | 10138496 A1 | 2/2003 |
| DE | 10229995 A1 | 1/2004 |
| EP | 1064087 A2 | 1/2001 |
| EP | 1371356 A2 | 12/2003 |
| EP | 1371357 A2 | 12/2003 |
| EP | 1371358 A2 | 12/2003 |
| FR | 2252840 A1 | 6/1975 |
| GB | 962919 A | 7/1964 |
| GB | 1333475 A | 10/1973 |
| GB | 1494915 A | 12/1977 |
| JP | 2006205129 A | 8/2006 |
| WO | WO-01/49817 A2 | 7/2001 |
| WO | WO-0239974 A1 | 5/2002 |
| WO | WO-0341675 A2 | 5/2003 |
| WO | WI-2014064255 A2 | 5/2014 |
| WO | WO-2014191171 A1 | 12/2014 |

OTHER PUBLICATIONS

U.S. Appl. No. 15/24,642, filed May 5, 2017.
U.S. Appl. No. 15/523,953, filed May 3, 2017.
International Preliminary Report on Patentability for International Application No. PCT/EP2015/078554 dated Jun. 6, 2017.
International Search Report for International Application No. PCT/EP2015/078554, dated Feb. 23, 2016.
Written Opinion of the International Searching Authority for Interntional Application No. PCT/EP2015/078554, dated Jun. 9, 2016.

* cited by examiner

*Primary Examiner* — Nicole P Babson
(74) *Attorney, Agent, or Firm* — Faegre Drinker Biddle & Reath LLP

(57) ABSTRACT

The present invention relates to microcapsules comprising a capsule core and a capsule shell wherein the capsule shell comprises a core surrounding layer of a polyvinyl alcohol and an adjacent layer of a polyoxazoline, a process of their production and their use.

14 Claims, No Drawings

MICROCAPSULES

CROSS-REFERENCE TO RELATED APPLICATIONS

This application is a national stage application (under 35 U.S.C. § 371) of PCT/EP2015/078554, filed Dec. 3, 2015, which claims benefit of European Application No. 14196271.2, filed Dec. 4, 2014, both of which are incorporated herein by reference in their entirety.

The present invention relates to microcapsules comprising a capsule core and a capsule shell wherein the capsule shell comprises a core-surrounding layer of a polyvinyl alcohol and an adjacent layer of a polyoxazoline. The invention further relates to a process of their production and their use.

Microcapsules are known in a wide variety of embodiments and are used for very different purposes according to capsule shell tightness. They serve to protect core materials which are not to be released until there is a mechanical impact which destroys the capsule shell, for example dyes for carbonless copy papers, or encapsulated scents. Capsule shell materials in such application areas are known to be based on gelatin, polyurethane resin, melamine-formaldehyde resin or polyacrylate. Furthermore, the impact releasing the active ingredient may be a thermal or magnetic one.

Coacervation is a well known microencapsulation method. According to such a process a water soluble polymer is deposited by phase separation from its solution by the addition of a second solvent which reduces its solubility. A well-known system is polyvinylalcohol/-1 propanol.

It is further known to produce microcapsules via a complex coacervation method. The shell building process is based on the principle of neutralization of opposite charged colloids in an aqueous solution. An example for complex coacervation is positively charged gelatin and negatively charged gum arabicum.

EP-A 1 064 087 teaches the production of microcapsules having pervious shells wherein an organic microsphere is enveloped with alternating layers of cationic and anionic polyelectrolytes and the microsphere is subsequently dissolved out to leave a cavity or void space.

JP2006-205129 teaches a method of producing microcapsules using a hydrophilic colloid as a basic film substance which comprises a carboxyl group, like gelatin, and hardening the basic film substance with a compound which has an oxazoline group for the formation of the shell. This compound comprising an oxazoline group is preferably a high molecular compound.

WO 2014/064255 teaches microcapsules comprising a shell of a polycarboxylic acid like polyacrylic acid or copolymers like ethylene-maleic anhydride surrounding the core and optionally an interposed layer which interacts with the polycarboxylic acid. Poly(2-ethyl-2-oxazoline) and polyvinylalcohol are mentioned among others as polymeric material forming said interposed layer. Exemplified are microcapsules comprising an inner layer of poly(methacrylic acid) and a second layer of poly(vinyl pyrrolidone). According to this teaching it is necessary to build several layers in order to obtain good microcapsules.

It is therefore an object of the present invention to find an alternative shell material which is easy to handle and also an advantageous process for producing these microcapsules. Microcapsules with such a shell material should if required have a good tightness and offer various options for the release of the core material.

It is an aspect of the present invention to provide microcapsules which exhibit a good storage stability.

Accordingly, microcapsules comprising a capsule core and a capsule shell wherein the capsule shell comprises a core surrounding layer of a polyvinyl alcohol and an adjacent layer of a polyoxazoline have been found.

Preferably, the capsule shell consists of a core-surrounding layer of an anionic polyvinyl alcohol.

Furthermore, a process for producing microcapsules comprising a capsule shell and a capsule core has been found, comprising the process steps:

a) preparation of an oil-in-water emulsion with a disperse phase which comprises the core material and an aqueous continuous phase and a polyvinyl alcohol and
b) subsequent addition of one or more polyoxazoline(s).

The present invention further relates to the use of these microcapsules in cosmetic compositions, e.g. for the preparation of sunscreen compositions which comprise the active, i.e. the UV filter as capsule core of microcapsules or in applications in which the capsule core material is to be released by diffusion or targeted mechanically or by thermal destruction.

The microcapsules of the present invention comprise a capsule core and a capsule shell comprising a surrounding layer of a polyvinyl alcohol and an adjacent layer of a polyoxazoline. The capsule core comprises predominantly more than 95% by weight of the core material, which might be a single compound or a mixture of two or more compounds. The capsule core might be solid or liquid depending on the temperature and the melting point of the core material. Preferred is a capsule core, which is liquid at a temperature of 20° C. and normal pressure. Liquid means that the core material has a Brookfield viscosity of ≤5 Pa·s.

The average particle size of the capsules (Z-average by light scattering) is in the range from 0.5 to 80 µm, preferably in the range from 1 to 50 µm and in particular in the range from 1 to 30 µm. The weight ratio of capsule core to capsule shell is generally in the range from 50:50 to 95:5. A core/shell ratio in the range from 70:30 to 93:7 is preferred.

Suitable core materials for the microcapsules are substances that are insoluble to essentially insoluble in water. In the context of the present invention, "essentially insoluble in water" is to be understood as meaning a solubility of the core material in water of <25 g/l, preferably ≤5 g/l, at 25° C. If the core material is a mixture, this may be in the form of a solution or suspension.

Core materials are preferably selected from the group comprising, preferably consisting of, aliphatic and aromatic hydrocarbon compounds, saturated or unsaturated $C_6$-$C_{30}$-fatty acids, fatty alcohols, $C_6$-$C_{30}$-fatty amines, $C_4$-$C_{30}$-mono-, $C_4$-$C_{30}$-di- and $C_4$-$C_{30}$-polyesters, primary, secondary or tertiary $C_4$-$C_{30}$-carboxamides, fatty acid esters, natural and synthetic waxes, halogenated hydrocarbons, natural oils, $C_3$-$C_{20}$-ketones, $C_3$-$C_{20}$-aldehydes, fragrances and aroma substances, vitamins and UV filters.

By way of example, the following may be mentioned:
a) aliphatic hydrocarbon compounds such as saturated or unsaturated $C_6$-$C_{40}$-hydrocarbons which are branched or linear, e.g. such as n-hexane, n-heptane, n-octane, n-nonane, n-decane, n-undecane, n-dodecane, n-tetradecane, n-pentadecane, n-hexadecane, n-heptadecane, n-octadecane, n-nonadecane, n-eicosane, n-heneicosane, n-docosane, n-tricosane, n-tetracosane, n-pentacosane, n-hexacosane, n-heptacosane, n-octacosane, white oils, and cyclic hydrocarbons, e.g. cyclohexane, cyclooctane, cyclodecane;

b) aromatic hydrocarbon compounds such as benzene, naphthalene, biphenyl, o- or m-terphenyl, $C_1$-$C_{40}$-alkyl-substituted aromatic hydrocarbons such as dodecylbenzene, tetradecylbenzene, hexadecylbenzene, hexylnaphthalene, decylnaphthalene and diisopropylnaphthalene;

c) saturated or unsaturated $C_6$-$C_{30}$-fatty acids such as lauric acid, stearic acid, oleic acid or behenic acid, preferably eutectic mixtures of decanoic acid with e.g. myristic acid, palmitic acid or lauric acid;

d) fatty alcohols such as lauryl alcohol, stearyl alcohol, oleyl alcohol, myristyl alcohol, cetyl alcohol, mixtures such as coconut fatty alcohol, and also the so-called oxo alcohols, which are obtained by hydroformylation of α-olefins and further reactions;

e) $C_6$-$C_{30}$-fatty amines, such as decylamine, dodecylamine, tetradecylamine or hexadecylamine;

f) $C_4$-$C_{30}$-mono-, $C_4$-$C_{30}$-di- and $C_4$-$C_{30}$-polyesters, such as $C_1$-$C_{10}$-alkyl esters of $C_1$-$C_{20}$-carboxylic acids, such as propyl palmitate, methyl stearate or methyl palmitate, and also preferably their eutectic mixtures or methyl cinnamate and primary, secondary or tertiary $C_4$-$C_{30}$-carboxamides, such as N-dimethyloctanamide and N-dimethyldecanamide;

g) natural and synthetic waxes, such as montanic acid waxes, montanic ester waxes, carnauba wax, polyethylene wax, oxidized waxes, polyvinyl ether wax, ethylene vinyl acetate wax or hard waxes by Fischer-Tropsch processes;

h) halogenated hydrocarbons, such as chloroparaffin, bromooctadecane, bromopentadecane, bromononadecane, bromoeicosane, bromodocosane;

i) natural oils such as peanut oil and soybean oil;

j) $C_3$-$C_{20}$-ketones and $C_3$-$C_{20}$-aldehydes;

m) fragrances and aroma substances, if appropriate as a mixture in the aforementioned core materials of groups a) to i) and j), as described in WO 01/49817, or in "Flavors and Fragrances", Ullmann's Encyclopedia of Industrial Chemistry, Wiley-VCH, 2002, to which reference is expressly made;

n) vitamins, if appropriate as a mixture in the aforementioned core materials of groups a) to i) and j), such as water-insoluble vitamins and provitamins are e.g. vitamin A, vitamin A acetate, vitamin D, vitamin E, tocopherol derivatives, such as tocopherol acetate and vitamin K;

o) UV-filters.

Preferably the UV filters (o) according to the present invention are oil soluble UV filters.

Typical oil-soluble UV filters according to the present invention are the following substances (INCI-names):

($o_1$) p-amino benzoic acid derivatives,
($o_2$) salicyl acid derivatives,
($o_3$) benzophenone derivates,
($o_4$) dibenzoylmethane derivatives,
($o_5$) diphenylacrylates,
($o_6$) 3-imidazol-4-yl-acryl acid and their esters;
($o_7$) benzofurane derivatives;
($o_8$) polymeric UV filters;
($o_9$) cinnamic acid derivatives;
($o_{10}$) camphor derivatives;
($o_{11}$) hydroxyphenyl triazine derivates;
($o_{12}$) benzotriazole derivatives;
($o_{13}$) trianilino-s-triazine derivatives;
($o_{14}$) menthyl o-aminobenzoates;
($o_{15}$) homosalates;
($o_{16}$) benzylidene malonates;
($o_{17}$) merocyanine derivatives;
($o_{18}$) phenylene bis diphenyl triazines;
($o_{19}$) imidazoline derivatives; and
($o_{20}$) diaryl butadiene derivatives.

Exemplified compounds for p-amino benzoic acid derivatives ($o_1$) are 4-aminobenzoic acid (PABA); ethyldihydroxypropyl-PABA of formula

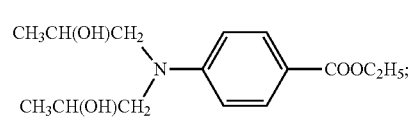
(PABA-01)

PEG-25-PABA of formula

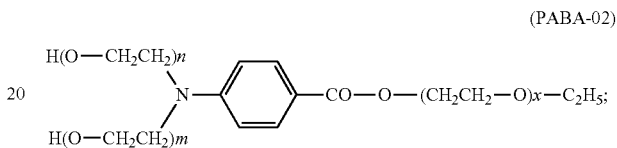
(PABA-02)

wherein m, n and x have the same meaning and are at most 25; octyldimethyl PABA of formula

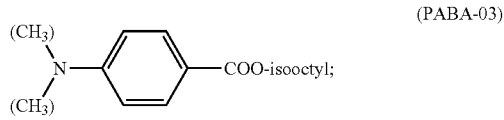
(PABA-03)

or glycyl aminobenzoate of formula

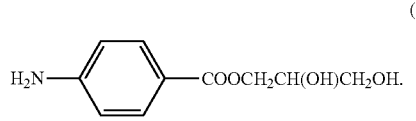
(PABA-04)

Exemplified compounds for salicylic acid derivatives ($o_2$) are Homomenthyl salicylate of formula

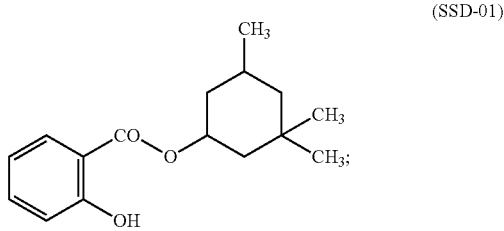 [SMILES: CC1CC(OC(=O)c2ccccc2O)CC(C)(C)C1]
(SSD-01)

tri-ethanolaminsalicylate of formula

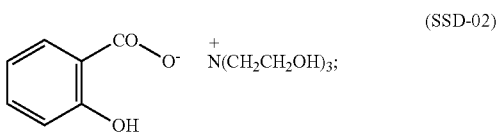
(SSD-02)

amyl-p-dimethylaminobenzoate of formula

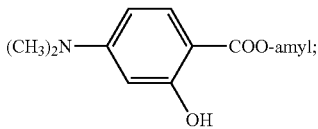
(SSD-03)

octyl salicylate of formula

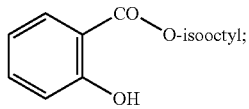
(SSD-04)

or 4-isopropylbenzyl salicy-salicylate of formula

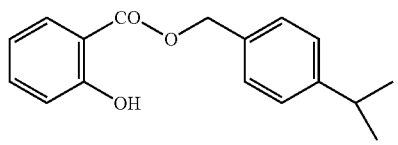
(SSD-05)

Exemplified compounds for benzophenone derivatives ($o_3$) are: benzophenone-3-(2-hydroxy-4-methoxybenzophenone); benzophenone-8-(2,2'-dihydroxy-4-methoxybenzophenone); or amino substituted hydroxybenzophenones of formula

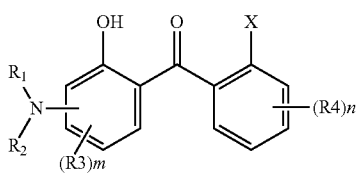
(HBP-01)

wherein
$R_1$ and $R_2$ are hydrogen, $C_1$-$C_{20}$alkyl, $C_2$-$C_{10}$alkenyl, $C_3$-$C_{10}$cycloalkyl, $C_3$-$C_{10}$cycloalkenyl, wherein the radicals $R_1$ und $R_2$ together with the $R_1$—N—$R_2$ nitrogen atom may form a 5- or 6-membered ring;
$R_3$ and $R_4$, independently from each other are $C_1$-$C_{20}$alkyl; $C_2$-$C_{10}$alkenyl; $C_3$-$C_{10}$cycloalkyl; $C_3$-$C_{10}$cycloalkenyl; $C_1$-$C_{22}$alkoxy; $C_1$-$C_{20}$alkoxycarbonyl; $C_1$-$C_{12}$alkylamino; $C_1$-$C_{12}$dialkylamino; optionally substituted aryl; heteroaryl;
X is hydrogen; COOR$_5$; or CONR$_6$R$_7$;
$R_5$, $R_6$, $R_7$, independently from each other are hydrogen; $C_1$-$C_{20}$alkyl; $C_2$-$C_{10}$alkenyl; $C_3$-$C_{10}$cycloalkyl; $C_3$-$C_{10}$cycloalkenyl; (Y—O)$_o$—Z; or aryl;
Y —(CH$_2$)$_2$—, —(CH$_2$)$_3$—, —CH$_2$)$_4$—, —CH(CH$_3$)—CH$_2$—;
Z is —CH$_2$—CH$_3$; —CH$_2$—CH$_2$—CH$_3$; —CH$_2$—CH$_2$—CH$_2$—CH$_3$; or —CH(CH$_3$)—CH$_3$;
m is 0 to 3;
n is 0 to 4; and
o 1 to 20.

Most preferred diethylamino hydroxybenzoyl hexyl benzoate corresponds to formula

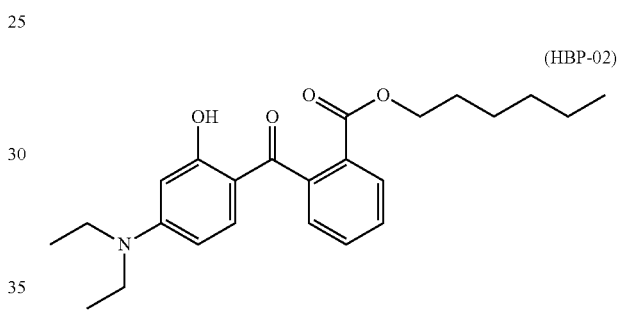
(HBP-02)

Exemplified dibenzoylmethane derivatives ($o_4$) are butyl-methoxydibenzoylmethane-[1-(4-tert.-butyl)-3-(4-methoxyphenyl)propan-1,3-dion].

Exemplified diphenylacrylate derivatives ($o_5$) are octocrylene-(2-ethylhexyl-2-cyano-3,3'-diphenylacrylate) or etocrylene-(ethyl-2-cyano-3,3'-diphenylacrylate).

Exemplified benzofurane derivatives ($o_7$) are 3-(benzofuranyl)-2-cyanoacrylate, 2-(2-benzofuranyl)-5-tert.-butylbenzoxazole or 2-(p-aminophenyl)benzofurane and most preferably the compounds of formula

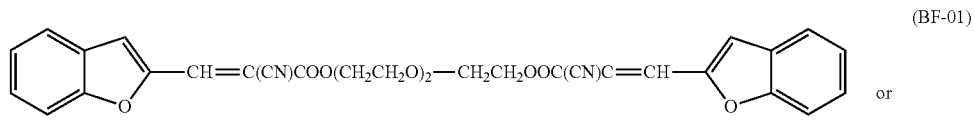
(BF-01)

or

(BF-02)

Exemplified polymeric UV filters (o₈), which comprise one or more silicium-organic radicals are benzylidenmalonate derivatives, preferably the compound of formula

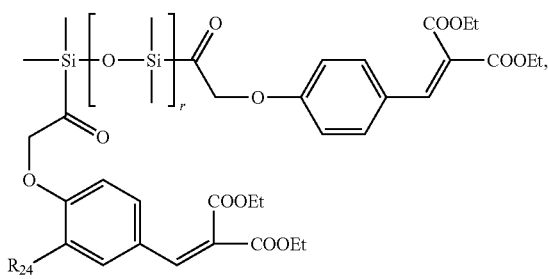
(PUV-01)

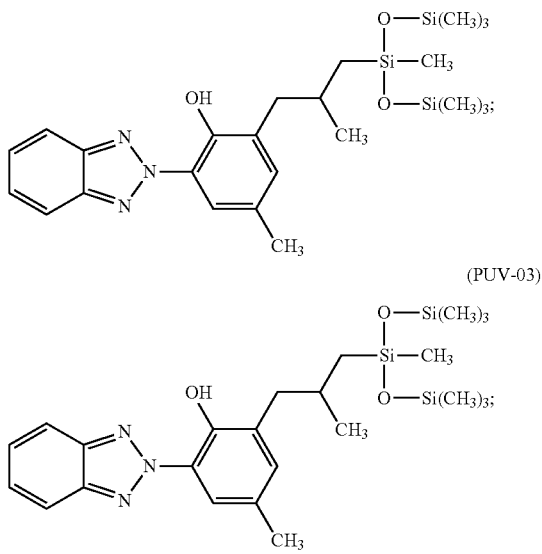
(PUV-02)

(PUV-03)

wherein
$R_{24}$ is hydrogen; or methoxy, and r is about 7; the compound of formula or polysilicone-15 according to formula

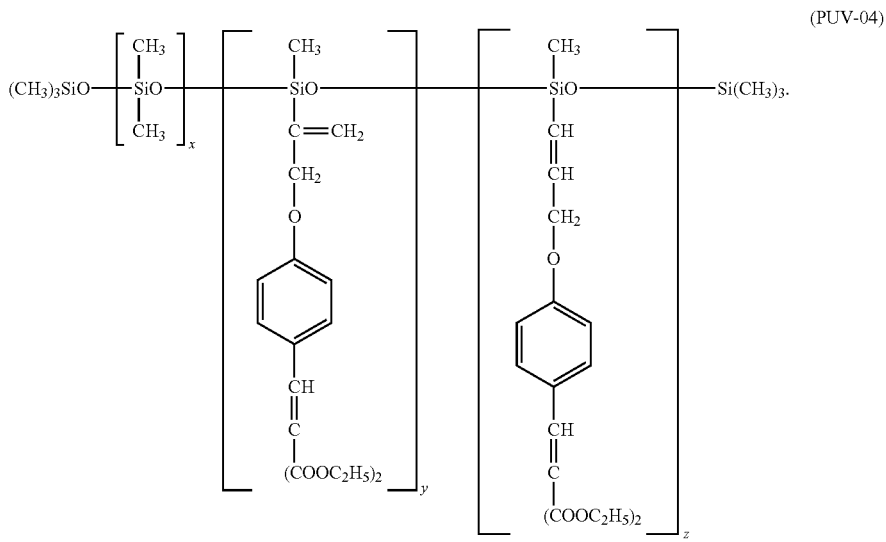
(PUV-04)

Exemplified cinnamic derivatives (o₉) are octylmethoxycinnamate (4-methoxy cinnamic acid-2-ethylhexylester), diethanolaminmethoxycinnamate (diethanolamine salt of 4-methoxy cinnamicacid), isoamyl p-methoxycinnamate (4-ethoxy cinnamic acid 2-isoamylester), 2,5-diisopropylmethylcinnamate or a cinnamic acid amido derivative.

Exemplified camphor derivatives (o₁₀) are 4-methyl-benzylidencamphor [3-(4'-methyl)benzylidene-bornan-2-on], 3-benzylidene camphor (3-benzylidene-bornan-2-on), polyacrylamidomethylbenzylidene camphor {N-[2(und 4)-2-oxyborn-3-ylidenmethyl)benzyl]acrylamid polymer}.

Exemplified hydroxyphenyl triazine derivatives (o₁₁) are preferably bis-resorcinyl-triazines of formula (HPT-01)

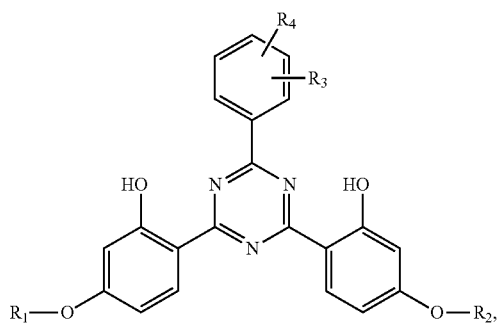

wherein $R_1$ and $R_2$, independently from each other are hydrogen; $C_1$-$C_{18}$alkyl; $C_2$-$C_{18}$alkenyl; a radical of formula —$CH_2$—$CH$(—$OH$)—$CH_2$—O-$T_1$; a radical of formula (HPT-01a)

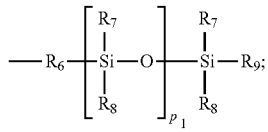

or a radical of formula (HPT-01h)

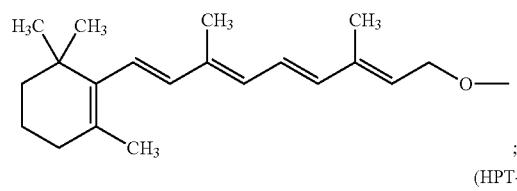

$R_3$, $R_4$ and $R_5$, independently from each other are hydroxy; $C_1$-$C_5$alkoxy or $C_1$-$C_5$alkoxy which is substituted by one or more OH-groups; amino; mono- or Di-$C_1$-$C_5$-alkylamino; a radical of formula (HPT-01b)

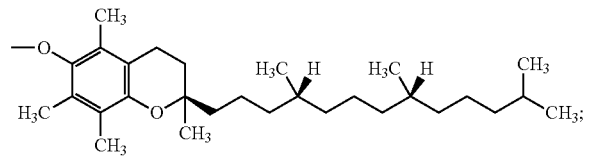

(HPT-01c)

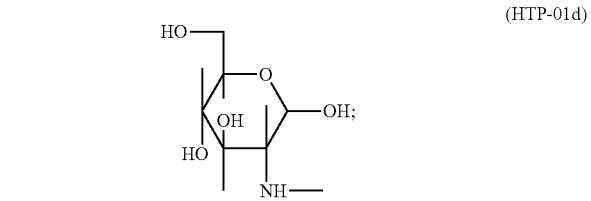

(HTP-01d)

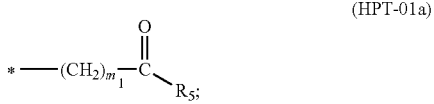

-continued (HPT-01e)

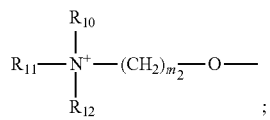

(HPT-01f)

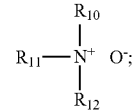

(HPT-01g)

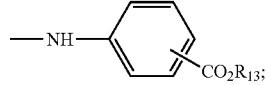

$R_{10}$, $R_{11}$ and $R_{12}$ independently from each other are $C_1$-$C_{14}$alkyl or $C_1$-$C_{14}$alkyl which is substituted by one or more OH groups;

$R_{13}$ is hydrogen; M; $C_1$-$C_5$alkyl; or a radical of formula —$(CH_2)_{m3}$-O-$T_1$ $R_6$ is the direct bond; straight- or branched $C_1$-$C_4$alkyl; or the radical of formula —$C_{m4}H_{2m4}$, or —$C_{m4}H_{2m4}$—O—;

$R_7$, $R_8$ and $R_9$, independently from each other are $C_1$-$C_{18}$alkyl; $C_1$-$C_{18}$Alkoxy or a radical of formula (HPT-01m)

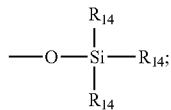

$R_{14}$ is $C_1$-$C_5$alkyl;

M is a metal cation;

$T_1$ is hydrogen; or $C_1$-$C_8$alkyl;

$m_1$, $m_2$ and $m_3$, independently from each other are a number from 1 to 3;

$m_4$ is a number from 2 to 14; and $p_1$ is 0; or a number from 1 bis 5.

Exemplified compounds of ($o_{11}$) are:

2-(4'-methoxyphenyl)-4,6-bis(2'-hydroxy-4'-n-octyloxy-phenyl)-1,3,5-triazine;

2,4-bis-{[4-(3-(2-propyloxy)-2-hydroxy-propyloxy)-2-hydroxy]-phenyl}-6-(4-methoxyphenyl)-1,3,5-triazine;

2,4-bis-{[4-(2-ethyl-hexyloxy)-2-hydroxy]-phenyl}-6-[4-(2-methoxyethyl-carboxyl)phenylamino]-1,3,5-triazine;

2,4-bis-{[4-(tris(trimethylsiloxy-silylpropyloxy)-2-hydroxy]-phenyl}-6-(4-methoxy-phenyl)-1,3,5-triazin;

2,4-bis-{[4-(2"methylpropenyloxy)-2-hydroxy]-phenyl}-6-(4-methoxyphenyl)-1,3,5-triazine;

2,4-bis-{[4-(1',1',1',3',5',5',5'-Heptamethyltrisilyl-2"-methyl-propyloxy)-2-hydroxy]-phenyl}-6-(4-methoxyphenyl)-1,3,5-triazine;

2,4-bis-{[4-(3-(2-propyloxy)-2-hydroxy-propyloxy)-2-hydroxy]-phenyl}-6-[4-ethylcarboxyl)-phenylamino]-1,3,5-triazine;

2,4-bis-{[4-(2-ethyl-hexyloxy)-2-hydroxy]-phenyl}-6-(1-methylpyrrol-2-yl)-1,3,5-triazine; or 2,2'-[6-(4-methoxyphenyl)-1,3,5-triazine-2,4-diyl]Bis[5-[(2-ethylhexyl)oxy]-(bis-ethylhexyloxyphenol methoxyphenyl triazine) according to formula

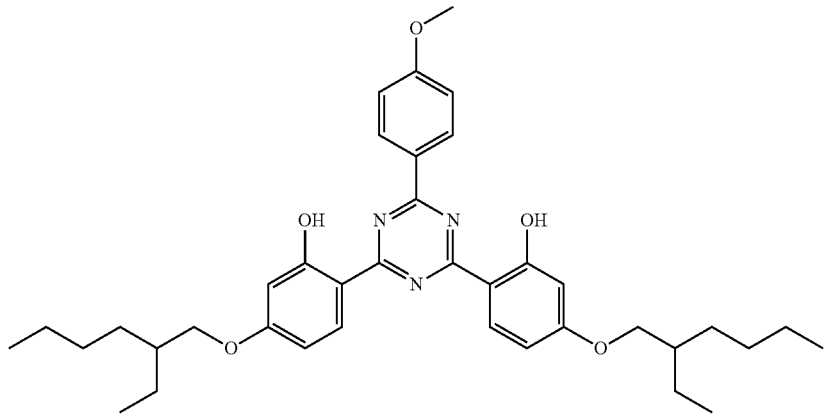
(BRT-02)

Exemplified benzotriazole derivatives ($o_{12}$) correspond to formula

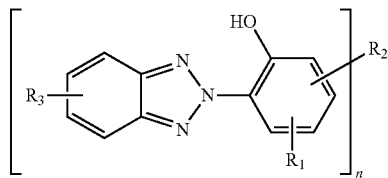
(BT-01)

wherein
$R_1$ is hydrogen; $C_1$-$C_{12}$alkyl; $C_1$-$C_{12}$alkoxy; $C_1$-$C_{12}$alkoxycarbonyl; $C_5$-$C_{10}$cycloalkyl;
$R_3$ is hydrogen; $C_1$-$C_{18}$alkyl; $C_1$-$C_{12}$alkoxy; or halogen; and
n is 1 or 2;
when n=1,
$R_2$ is $C_1$-$C_{20}$alkyl; $C_5$-$C_{10}$cyclo-$C_1$-$C_5$alkyl; $C_1$-$C_{12}$alkoxy-$C_1$-$C_5$alkyl; $C_5$-$C_{10}$cycloalkoxy-$C_1$-$C_5$alkyl; $C_6$-$C_{10}$aryl; $C_6$-$C_{10}$aryl-$C_1$-$C_5$alkyl;
when n=2,
$R_2$ is the direct bond; or —$(CH_2)_p$—; and
p is a number from 1 to 3.
Preferably compounds of formula (BT-01) are considered, wherein
$R_1$ is $C_1$-$C_{12}$alkyl;
$R_3$ is hydrogen; halogen, preferably Cl;
n is 1;
$R_2$ is $C_1$-$C_{12}$alkyl; and
p 1 to 3;
Mostly preferred are compounds of formula

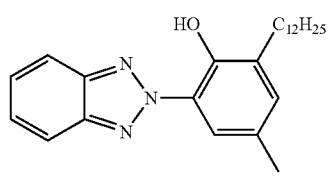
BT-02

Furthermore UV filters of formula BT-01 are preferred, wherein
$R_1$ is hydrogen;
$R_3$ is $C_1$-$C_{18}$alkyl;
n=2; and
$R_2$ is —$CH_2$—.

Exemplified trianilino-s-triazine derivatives ($o_{13}$) correspond to formula

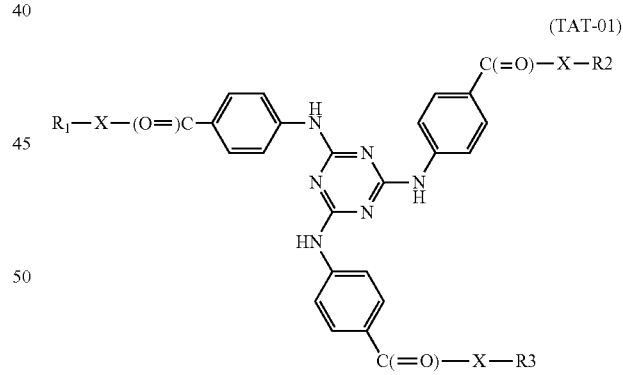
(TAT-01)

wherein
$R_1$, $R_2$ and $R_3$ independently from each other are optionally substituted $C_1$-$C_{20}$alkyl, aryl or heteroaryl,
X is O; or $NR_4$; and
$R_4$ is hydrogen; or optionally substituted $C_1$-$C_{20}$alkyl, aryl or heteroaryl.

Most preferred representatives of this class of compounds is Ethylhexyl Triazone corresponding to formula or Ethylhexyl Bis-Isopentylbenzoxazolylphenyl Melamine according to formula
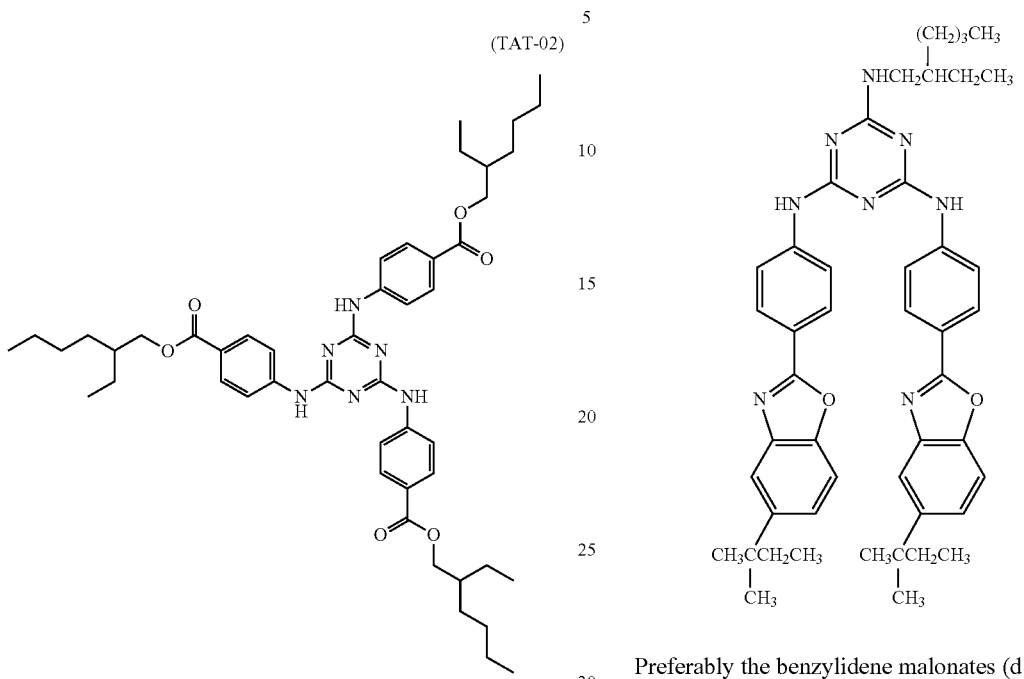
or Diethylhexyl Butamido Triazone according to formula
Preferably the benzylidene malonates (d₁₆) correspond to formula
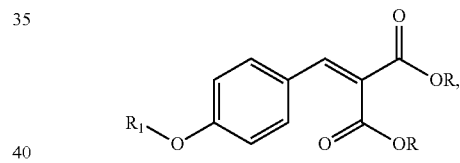
wherein
R₁ is methyl; ethyl; propyl; or n-butyl;
when R₁ is methyl, then
R is tert. Butyl;
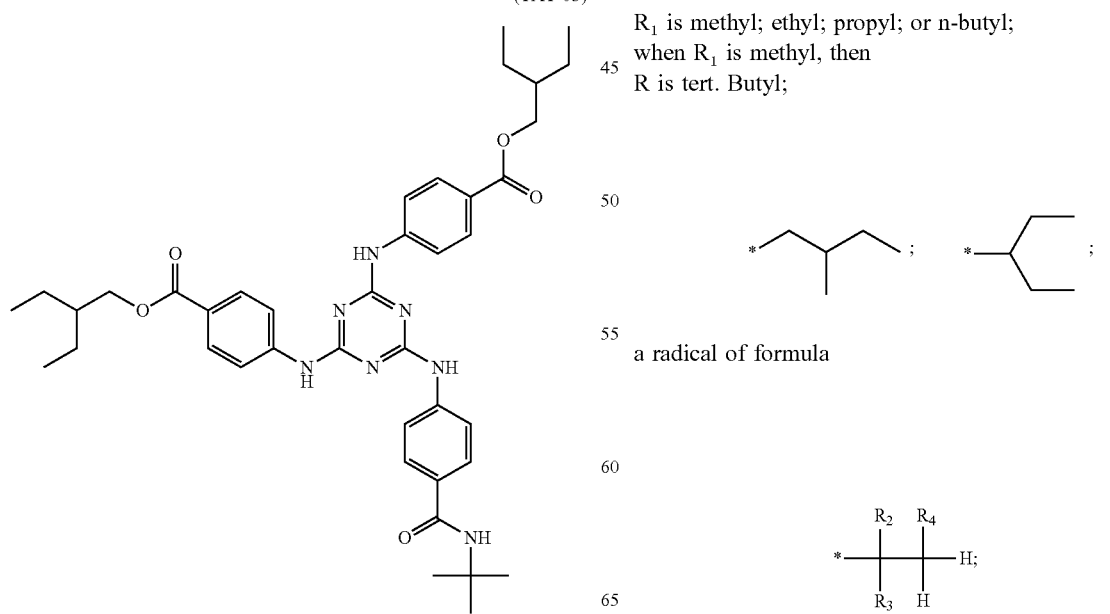
a radical of formula or a radical of formula

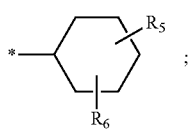
(MBM-01b)

wherein
R₂ and R₃, independently from each other are hydrogen; or methyl;
R₄ is methyl; ethyl; or n-propyl;
R₅ and R₆ independently from each other are hydrogen; or $C_1$-$C_3$alkyl;
when R₁ is ethyl; propyl; or n-butyl, than
R is isopropyl.

Most preferred benzylidene malonates ($o_{16}$) are listed in the table below:

TABLE 1

Examples for preferred benzylidenemalonates ($O_{16}$)

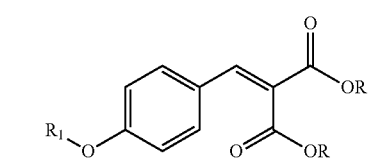

| | R₁ | R |
|---|---|---|
| (MBM-02) | methyl | |
| (MBM-03) | methyl | |
| (MBM-04) | methyl | |
| (MBM-05) | methyl | |
| (MBM-06) | methyl | |
| (MBM-07) | methyl | |
| (MBM-08) | methyl | |
| (MBM-09) | methyl | |
| (MBM-10) | methyl | |

TABLE 1-continued

Examples for preferred benzylidenemalonates ($O_{16}$)

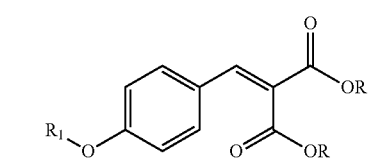

| | R₁ | R |
|---|---|---|
| (MBM-11) | ethyl |  |
| (MBM-12) | propyl |  |
| (MBM-13) | n-butyl |  |
| (MBM-14) | methyl | 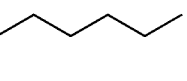 |
| (MBM-15) | methyl | 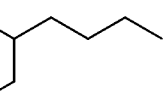 |

Exemplified compound for phenylene-bis-diphenyltriazines ($o_{18}$) is 5,6,5,6-tetraphenyl-3,3'-(1,4-phenylene)-bis[1,2,4]-triazine according to formula

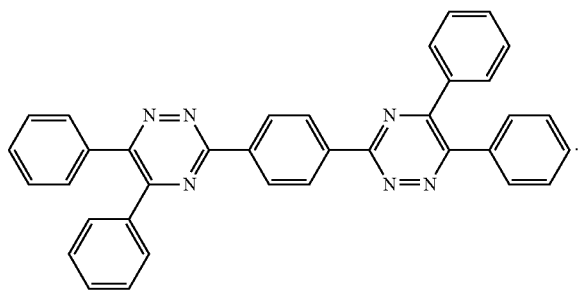
(PBT-01)

Exemplified compound for imidazoline derivatives ($o_{19}$) is Ethylhexyldimethoxybenzylidene-dioxo imidazoline propionate.

Exemplified compound for diarylbutadiene derivatives ($o_{20}$) is 1,1-Dicarboxy-(2, 2'-dimethylpropyl)-4, 4-diphenylbutadiene.

Each of the UV filters ($o_1$)-($o_{20}$) can be used as a mixture. For example, mixtures of two, three, four, five or six of the UV filter groups ($o_1$)-($o_{20}$) can be used according to the present invention.

Mostly preferred are the following oil-soluble UV filters (INCI names):
($o_{SOL-1}$) Benzophenone-3 (BP3);
($o_{SOL-2}$) Benzophenone-4 (BP4);

($o_{SOL-3}$) 3-Benzydilene Camphor (3BC);
($o_{SOL-4}$) Bis-Ethylhexyloxyphenol Methoxyphenyl Triazine (BEMT);
($o_{SOL-5}$) Butyl Methoxydibenzoylmethane (BMBM);
($o_{SOL-6}$) Diethylhexyl Butamido Triazone (DBT);
($o_{SOL-7}$) Drometrizole Trisiloxane (DTS);
($o_{SOL-8}$) Ethylhexyl Triazone (EHT);
($o_{SOL-9}$) Ethylhexyl Methoxycinnamate;
($o_{SOL-10}$) Benzylidene malonate (BM);
($o_{SOL-11}$) Diethylamino Hydroxy Benzoyl Hexyl Benzoate (DHHB);
($o_{SOL-12}$) Octocrylene;
($o_{SOL-13}$) Polysilicon-15;
($o_{SOL-14}$) Homosalate; and
($o_{SOL-15}$) Ethylhexyl salicylate.

Most preferred are oil-soluble UV filter mixtures consisting of ($o_{SOL-9}$) Ethylhexyl Methoxycinnamate,
($o_{SOL-4}$) Bis-Ethylhexyloxyphenol Methoxyphenyl Triazine,
($o_{SOL-8}$) Ethylhexyl Triazone and
($o_{SOL-11}$) Diethylamino Hydroxy Benzoyl Hexyl Benzoate.

In the table below possible UV filter mixtures from oil soluble UV filters (UV SOL 1 UV SQL 551) are listed:

TABLE 2

List of oil soluble organic UV-Filter-combinations

| | BP3 | BP4 | 3BC | BEMT | BMBM | DBT | DTS | EHT | MBC | EMC | BMP | DHHB |
|---|---|---|---|---|---|---|---|---|---|---|---|---|
| 1-Filter combinations ||||||||||||||
| UV OIL-SOL 1 | x | | | | | | | | | | | |
| UV OIL-SOL 2 | | x | | | | | | | | | | |
| UV OIL-SOL 3 | | | x | | | | | | | | | |
| UV OIL-SOL 4 | | | | x | | | | | | | | |
| UV OIL-SOL 5 | | | | | x | | | | | | | |
| UV OIL-SOL 6 | | | | | | x | | | | | | |
| UV OIL-SOL 7 | | | | | | | x | | | | | |
| UV OIL-SOL 8 | | | | | | | | x | | | | |
| UV OIL-SOL 9 | | | | | | | | | x | | | |
| UV OIL-SOL 10 | | | | | | | | | | x | | |
| UV OIL-SOL 11 | | | | | | | | | | | x | |
| UV OIL-SOL 12 | | | | | | | | | | | | x |
| 2-Filter combinations ||||||||||||||
| UV OIL-SOL 13 | x | x | | | | | | | | | | |
| UV OIL-SOL 14 | x | | x | | | | | | | | | |
| UV OIL-SOL 15 | x | | | x | | | | | | | | |
| UV OIL-SOL 16 | x | | | | x | | | | | | | |
| UV OIL-SOL 17 | x | | | | | x | | | | | | |
| UV OIL-SOL 18 | x | | | | | | x | | | | | |
| UV OIL-SOL 19 | x | | | | | | | x | | | | |
| UV OIL-SOL 20 | x | | | | | | | | x | | | |
| UV OIL-SOL 21 | x | | | | | | | | | x | | |
| UV OIL-SOL 22 | x | | | | | | | | | | x | |
| UV OIL-SOL 23 | x | | | | | | | | | | | x |
| UV OIL-SOL 24 | | x | x | | | | | | | | | |
| UV OIL-SOL 25 | | x | | x | | | | | | | | |
| UV OIL-SOL 26 | | x | | | x | | | | | | | |
| UV OIL-SOL 27 | | x | | | | x | | | | | | |
| UV OIL-SOL 28 | | x | | | | | x | | | | | |
| UV OIL-SOL 29 | | x | | | | | | x | | | | |
| UV OIL-SOL 30 | | x | | | | | | | x | | | |
| UV OIL-SOL 31 | | x | | | | | | | | x | | |
| UV OIL-SOL 32 | | x | | | | | | | | | x | |
| UV OIL-SOL 33 | | x | | | | | | | | | | x |
| UV OIL-SOL 34 | | | x | x | | | | | | | | |
| UV OIL-SOL 35 | | | x | | x | | | | | | | |
| UV OIL-SOL 36 | | | x | | | x | | | | | | |
| UV OIL-SOL 37 | | | x | | | | x | | | | | |
| UV OIL-SOL 38 | | | x | | | | | x | | | | |
| UV OIL-SOL 39 | | | x | | | | | | x | | | |
| UV OIL-SOL 40 | | | x | | | | | | | x | | |
| UV OIL-SOL 41 | | | x | | | | | | | | x | |
| UV OIL-SOL 42 | | | x | | | | | | | | | x |
| UV OIL-SOL 43 | | | | x | x | | | | | | | |
| UV OIL-SOL 44 | | | | x | | x | | | | | | |
| UV OIL-SOL 45 | | | | x | | | x | | | | | |
| UV OIL-SOL 46 | | | | x | | | | x | | | | |
| UV OIL-SOL 47 | | | | x | | | | | x | | | |
| UV OIL-SOL 48 | | | | x | | | | | | x | | |
| UV OIL-SOL 49 | | | | x | | | | | | | x | |
| UV OIL-SOL 50 | | | | x | | | | | | | | x |
| UV OIL-SOL 51 | | | | | x | x | | | | | | |
| UV OIL-SOL 52 | | | | | x | | x | | | | | |
| UV OIL-SOL 53 | | | | | x | | | x | | | | |
| UV OIL-SOL 54 | | | | | x | | | | x | | | |

TABLE 2-continued

List of oil soluble organic UV-Filter-combinations

| | Abbreviations | | | | | | | | | | | |
|---|---|---|---|---|---|---|---|---|---|---|---|---|
| | BP3 | BP4 | 3BC | BEMT | BMBM | DBT | DTS | EHT | MBC | EMC | BMP | DHHB |
| UV OIL-SOL 55 | | | | | x | | | | x | | | |
| UV OIL-SOL 56 | | | | | x | | | | | x | | |
| UV OIL-SOL 57 | | | | | x | | | | | | | x |
| UV OIL-SOL 58 | | | | | | x | x | | | | | |
| UV OIL-SOL 59 | | | | | | x | | x | | | | |
| UV OIL-SOL 60 | | | | | | x | | | x | | | |
| UV OIL-SOL 61 | | | | | | x | | | | x | | |
| UV OIL-SOL 62 | | | | | | x | | | | | x | |
| UV OIL-SOL 63 | | | | | | x | | | | | | x |
| UV OIL-SOL 64 | | | | | | | x | x | | | | |
| UV OIL-SOL 65 | | | | | | | x | | x | | | |
| UV OIL-SOL 66 | | | | | | | x | | | x | | |
| UV OIL-SOL 67 | | | | | | | x | | | | x | |
| UV OIL-SOL 68 | | | | | | | x | | | | | x |
| UV OIL-SOL 69 | | | | | | | | x | x | | | |
| UV OIL-SOL 70 | | | | | | | | x | | x | | |
| UV OIL-SOL 71 | | | | | | | | x | | | x | |
| UV OIL-SOL 72 | | | | | | | | x | | | | x |
| UV OIL-SOL 73 | | | | | | | | | x | x | | |
| UV OIL-SOL 74 | | | | | | | | | x | | x | |
| UV OIL-SOL 75 | | | | | | | | | x | | | x |
| UV OIL-SOL 76 | | | | | | | | | | x | x | |
| UV OIL-SOL 77 | | | | | | | | | | x | | x |
| UV OIL-SOL 78 | | | | | | | | | | | x | x |

3-Filter combinations

| | BP3 | BP4 | 3BC | BEMT | BMBM | DBT | DTS | EHT | MBC | EMC | BMP | DHHB |
|---|---|---|---|---|---|---|---|---|---|---|---|---|
| UV OIL-SOL 79 | x | x | x | | | | | | | | | |
| UV OIL-SOL 80 | x | x | | x | | | | | | | | |
| UV OIL-SOL 81 | x | x | | | x | | | | | | | |
| UV OIL-SOL 82 | x | x | | | | x | | | | | | |
| UV OIL-SOL 83 | x | x | | | | | x | | | | | |
| UV OIL-SOL 84 | x | x | | | | | | x | | | | |
| UV OIL-SOL 86 | x | x | | | | | | | x | | | |
| UV OIL-SOL 87 | x | x | | | | | | | | x | | |
| UV OIL-SOL 88 | x | x | | | | | | | | | x | |
| UV OIL-SOL 89 | x | x | | | | | | | | | | x |
| UV OIL-SOL 90 | x | | x | x | | | | | | | | |
| UV OIL-SOL 91 | x | | x | | x | | | | | | | |
| UV OIL-SOL 92 | x | | x | | | x | | | | | | |
| UV OIL-SOL 93 | x | | x | | | | x | | | | | |
| UV OIL-SOL 94 | x | | x | | | | | x | | | | |
| UV OIL-SOL 95 | x | | x | | | | | | x | | | |
| UV OIL-SOL 96 | x | | x | | | | | | | x | | |
| UV OIL-SOL 97 | x | | x | | | | | | | | x | |
| UV OIL-SOL 98 | x | | x | | | | | | | | | x |
| UV OIL-SOL 99 | x | | | x | x | | | | | | | |
| UV OIL-SOL 100 | x | | | x | | x | | | | | | |
| UV OIL-SOL 101 | x | | | x | | | x | | | | | |
| UV OIL-SOL 102 | x | | | x | | | | x | | | | |
| UV OIL-SOL 103 | x | | | x | | | | | x | | | |
| UV OIL-SOL 104 | x | | | x | | | | | | x | | |
| UV OIL-SOL 105 | x | | | x | | | | | | | x | |
| UV OIL-SOL 106 | x | | | x | | | | | | | | x |
| UV OIL-SOL 107 | x | | | | x | x | | | | | | |
| UV OIL-SOL 108 | x | | | | x | | x | | | | | |
| UV OIL-SOL 109 | x | | | | x | | | x | | | | |
| UV OIL-SOL 110 | x | | | | x | | | | x | | | |
| UV OIL-SOL 111 | x | | | | x | | | | | x | | |
| UV OIL-SOL 112 | x | | | | x | | | | | | x | |
| UV OIL-SOL 113 | x | | | | x | | | | | | | x |
| UV OIL-SOL 114 | x | | | | | x | x | | | | | |
| UV OIL-SOL 115 | x | | | | | x | | x | | | | |
| UV OIL-SOL 116 | x | | | | | x | | | x | | | |
| UV OIL-SOL 117 | x | | | | | x | | | | x | | |
| UV OIL-SOL 118 | x | | | | | x | | | | | x | |
| UV OIL-SOL 119 | x | | | | | x | | | | | | x |
| UV OIL-SOL 120 | x | | | | | | x | x | | | | |
| UV OIL-SOL 121 | x | | | | | | x | | x | | | |
| UV OIL-SOL 122 | x | | | | | | x | | | x | | |
| UV OIL-SOL 123 | x | | | | | | x | | | | x | |
| UV OIL-SOL 124 | x | | | | | | x | | | | | x |
| UV OIL-SOL 125 | x | | | | | | | x | x | | | |
| UV OIL-SOL 126 | x | | | | | | | x | | x | | |
| UV OIL-SOL 127 | x | | | | | | | x | | | x | |

TABLE 2-continued

List of oil soluble organic UV-Filter-combinations

| | BP3 | BP4 | 3BC | BEMT | BMBM | DBT | DTS | EHT | MBC | EMC | BMP | DHHB |
|---|---|---|---|---|---|---|---|---|---|---|---|---|
| UV OIL-SOL 128 | x | | | | | | | x | | | | x |
| UV OIL-SOL 129 | x | | | | | | | x | x | | | |
| UV OIL-SOL 130 | x | | | | | | | x | | x | | |
| UV OIL-SOL 131 | x | | | | | | | x | | | | x |
| UV OIL-SOL 132 | x | | | | | | | | x | x | | |
| UV OIL-SOL 133 | x | | | | | | | | x | | | x |
| UV OIL-SOL 134 | x | | | | | | | | | x | | x |
| UV OIL-SOL 135 | | x | x | x | | | | | | | | |
| UV OIL-SOL 136 | | x | x | | x | | | | | | | |
| UV OIL-SOL 137 | | x | x | | | x | | | | | | |
| UV OIL-SOL 138 | | x | x | | | | x | | | | | |
| UV OIL-SOL 139 | | x | x | | | | | x | | | | |
| UV OIL-SOL 140 | | x | x | | | | | | x | | | |
| UV OIL-SOL 141 | | x | x | | | | | | | x | | |
| UV OIL-SOL 142 | | x | x | | | | | | | | x | |
| UV OIL-SOL 143 | | x | x | | | | | | | | | x |
| UV OIL-SOL 144 | | x | | x | x | | | | | | | |
| UV OIL-SOL 145 | | x | | x | | x | | | | | | |
| UV OIL-SOL 146 | | x | | x | | | x | | | | | |
| UV OIL-SOL 147 | | x | | x | | | | x | | | | |
| UV OIL-SOL 148 | | x | | x | | | | | x | | | |
| UV OIL-SOL 149 | | x | | x | | | | | | x | | |
| UV OIL-SOL 150 | | x | | x | | | | | | | x | |
| UV OIL-SOL 151 | | x | | x | | | | | | | | x |
| UV OIL-SOL 152 | | x | | | x | x | | | | | | |
| UV OIL-SOL 153 | | x | | | x | | x | | | | | |
| UV OIL-SOL 154 | | x | | | x | | | x | | | | |
| UV OIL-SOL 155 | | x | | | x | | | | x | | | |
| UV SOL 156 | | x | | | x | | | | | x | | |
| UV OIL-SOL 157 | | x | | | x | | | | | | x | |
| UV OIL-SOL 158 | | x | | | x | | | | | | | x |
| UV OIL-SOL 159 | | x | | | | x | x | | | | | |
| UV OIL-SOL 160 | | x | | | | x | | x | | | | |
| UV OIL-SOL 161 | | x | | | | x | | | x | | | |
| UV OIL-SOL 162 | | x | | | | x | | | | x | | |
| UV OIL-SOL 163 | | x | | | | x | | | | | x | |
| UV OIL-SOL 164 | | x | | | | x | | | | | | x |
| UV OIL-SOL 165 | | x | | | | | x | x | | | | |
| UV OIL-SOL 166 | | x | | | | | x | | x | | | |
| UV OIL-SOL 167 | | x | | | | | x | | | x | | |
| UV OIL-SOL 168 | | x | | | | | x | | | | x | |
| UV OIL-SOL 169 | | x | | | | | x | | | | | x |
| UV OIL-SOL 170 | | x | | | | | | x | x | | | |
| UV OIL-SOL 171 | | x | | | | | | x | | x | | |
| UV OIL-SOL 172 | | x | | | | | | x | | | x | |
| UV OIL-SOL 173 | | x | | | | | | x | | | | x |
| UV OIL-SOL 174 | | x | | | | | | | x | x | | |
| UV OIL-SOL 175 | | x | | | | | | | x | | x | |
| UV OIL-SOL 176 | | x | | | | | | | x | | | x |
| UV OIL-SOL 177 | | x | | | | | | | | x | x | |
| UV OIL-SOL 178 | | x | | | | | | | | x | | x |
| UV OIL-SOL 179 | | x | | | | | | | | | x | x |
| UV OIL-SOL 180 | | | x | x | x | | | | | | | |
| UV OIL-SOL 181 | | | x | x | | x | | | | | | |
| UV OIL-SOL 182 | | | x | x | | | x | | | | | |
| UV OIL-SOL 183 | | | x | x | | | | x | | | | |
| UV OIL-SOL 184 | | | x | x | | | | | x | | | |
| UV OIL-SOL 185 | | | x | x | | | | | | x | | |
| UV OIL-SOL 186 | | | x | x | | | | | | | x | |
| UV OIL-SOL 187 | | | x | x | | | | | | | | x |
| UV OIL-SOL 188 | | | x | | x | x | | | | | | |
| UV OIL-SOL 189 | | | x | | x | | x | | | | | |
| UV OIL-SOL 190 | | | x | | x | | | x | | | | |
| UV OIL-SOL 191 | | | x | | x | | | | x | | | |
| UV OIL-SOL 192 | | | x | | x | | | | | x | | |
| UV OIL-SOL 193 | | | x | | x | | | | | | x | |
| UV OIL-SOL 194 | | | x | | x | | | | | | | x |
| UV OIL-SOL 195 | | | x | | | x | x | | | | | |
| UV OIL-SOL 196 | | | x | | | x | | x | | | | |
| UV OIL-SOL 197 | | | x | | | x | | | x | | | |
| UV OIL-SOL 198 | | | x | | | x | | | | x | | |
| UV OIL-SOL 199 | | | x | | | x | | | | | x | |
| UV OIL-SOL 200 | | | x | | | x | | | | | | x |
| UV OIL-SOL 201 | | | x | | | | x | x | | | | |

TABLE 2-continued

List of oil soluble organic UV-Filter-combinations

| | BP3 | BP4 | 3BC | BEMT | BMBM | DBT | DTS | EHT | MBC | EMC | BMP | DHHB |
|---|---|---|---|---|---|---|---|---|---|---|---|---|
| UV OIL-SOL 202 | | | x | | | | x | | x | | | |
| UV OIL-SOL 203 | | | x | | | | x | | | x | | |
| UV OIL-SOL 204 | | | x | | | | x | | | | x | |
| UV OIL-SOL 205 | | | x | | | | x | | | | | x |
| UV OIL-SOL 206 | | | x | | | | | x | x | | | |
| UV OIL-SOL 207 | | | x | | | | | x | | x | | |
| UV OIL-SOL 208 | | | x | | | | | x | | | x | |
| UV OIL-SOL 209 | | | x | | | | | x | | | | x |
| UV OIL-SOL 210 | | | x | | | | | | x | x | | |
| UV OIL-SOL 211 | | | x | | | | | | x | | x | |
| UV OIL-SOL 212 | | | x | | | | | | x | | | x |
| UV OIL-SOL 213 | | | x | | | | | | | x | x | |
| UV SOL 214 | | | x | | | | | | | x | | x |
| UV OIL-SOL 215 | | | x | | | | | | | | x | x |
| UV OIL-SOL 216 | | | | x | x | x | | | | | | |
| UV OIL-SOL 217 | | | | x | x | | x | | | | | |
| UV OIL-SOL 218 | | | | x | x | | | x | | | | |
| UV OIL-SOL 219 | | | | x | x | | | | x | | | |
| UV OIL-SOL 220 | | | | x | x | | | | | x | | |
| UV OIL-SOL 221 | | | | x | x | | | | | | x | |
| UV OIL-SOL 222 | | | | x | x | | | | | | | x |
| UV OIL-SOL 223 | | | | x | | x | x | | | | | |
| UV OIL-SOL 224 | | | | x | | x | | x | | | | |
| UV OIL-SOL 225 | | | | x | | x | | | x | | | |
| UV OIL-SOL 226 | | | | x | | x | | | | x | | |
| UV OIL-SOL 227 | | | | x | | x | | | | | x | |
| UV OIL-SOL 228 | | | | x | | x | | | | | | x |
| UV OIL-SOL 229 | | | | x | | | x | x | | | | |
| UV OIL-SOL 230 | | | | x | | | x | | x | | | |
| UV OIL-SOL 231 | | | | x | | | x | | | x | | |
| UV OIL-SOL 232 | | | | x | | | x | | | | x | |
| UV OIL-SOL 233 | | | | x | | | x | | | | | x |
| UV OIL-SOL 234 | | | | x | | | | x | x | | | |
| UV OIL-SOL 235 | | | | x | | | | x | | x | | |
| UV OIL-SOL 236 | | | | x | | | | x | | | x | |
| UV OIL-SOL 237 | | | | x | | | | x | | | | x |
| UV OIL-SOL 238 | | | | x | | | | | x | x | | |
| UV OIL-SOL 239 | | | | x | | | | | x | | x | |
| UV OIL-SOL 240 | | | | x | | | | | x | | | x |
| UV OIL-SOL 241 | | | | x | | | | | | x | x | |
| UV OIL-SOL 242 | | | | x | | | | | | x | | x |
| UV OIL-SOL 243 | | | | x | | | | | | | x | x |
| UV OIL-SOL 244 | | | | | x | x | x | | | | | |
| UV OIL-SOL 245 | | | | | x | x | | x | | | | |
| UV OIL-SOL 246 | | | | | x | x | | | x | | | |
| UV OIL-SOL 247 | | | | | x | x | | | | x | | |
| UV OIL-SOL 248 | | | | | x | x | | | | | x | |
| UV OIL-SOL 249 | | | | | x | x | | | | | | x |
| UV OIL-SOL 250 | | | | | x | | x | x | | | | |
| UV OIL-SOL 251 | | | | | x | | x | | x | | | |
| UV OIL-SOL 252 | | | | | x | | x | | | x | | |
| UV OIL-SOL 253 | | | | | x | | x | | | | x | |
| UV OIL-SOL 254 | | | | | x | | x | | | | | x |
| UV OIL-SOL 255 | | | | | x | | | x | x | | | |
| UV OIL-SOL 256 | | | | | x | | | x | | x | | |
| UV OIL-SOL 257 | | | | | x | | | x | | | x | |
| UV OIL-SOL 258 | | | | | x | | | x | | | | x |
| UV OIL-SOL 259 | | | | | x | | | | x | x | | |
| UV OIL-SOL 260 | | | | | x | | | | x | | x | |
| UV OIL-SOL 261 | | | | | x | | | | x | | | x |
| UV OIL-SOL 262 | | | | | x | | | | | x | x | |
| UV OIL-SOL 263 | | | | | x | | | | | x | | x |
| UV OIL-SOL 264 | | | | | x | | | | | | x | x |
| UV OIL-SOL 265 | | | | | | x | x | x | | | | |
| UV OIL-SOL 266 | | | | | | x | x | | x | | | |
| UV OIL-SOL 267 | | | | | | x | x | | | x | | |
| UV OIL-SOL 268 | | | | | | x | x | | | | x | |
| UV OIL-SOL 289 | | | | | | x | x | | | | | x |
| UV OIL-SOL 290 | | | | | | x | | x | x | | | |
| UV OIL-SOL 291 | | | | | | x | | x | | x | | |
| UV OIL-SOL 292 | | | | | | x | | x | | | x | |
| UV OIL-SOL 293 | | | | | | x | | x | | | | x |
| UV OIL-SOL 294 | | | | | | x | | | x | x | | |
| UV OIL-SOL 295 | | | | | | x | | | x | | x | |

TABLE 2-continued

List of oil soluble organic UV-Filter-combinations

| | BP3 | BP4 | 3BC | BEMT | BMBM | DBT | DTS | EHT | MBC | EMC | BMP | DHHB |
|---|---|---|---|---|---|---|---|---|---|---|---|---|
| UV OIL-SOL 296 | | | | | | x | | x | | | | x |
| UV OIL-SOL 297 | | | | | | x | | | x | x | | |
| UV OIL-SOL 298 | | | | | | x | | | x | | | x |
| UV OIL-SOL 299 | | | | | | x | | | | | x | x |
| UV OIL-SOL 300 | | | | | | | x | x | x | | | |
| UV OIL-SOL 301 | | | | | | | x | x | | x | | |
| UV OIL-SOL 302 | | | | | | | x | x | | | x | |
| UV OIL-SOL 303 | | | | | | | x | x | | | | x |
| UV OIL-SOL 304 | | | | | | | x | | x | x | | |
| UV OIL-SOL 305 | | | | | | | x | | x | | x | |
| UV OIL-SOL 306 | | | | | | | x | | x | | | x |
| UV OIL-SOL 307 | | | | | | | x | | | x | x | |
| UV OIL-SOL 308 | | | | | | | x | | | x | | X |
| UV OIL-SOL 309 | | | | | | | x | | | | x | x |
| UV OIL-SOL 310 | | | | | | | | x | x | x | | |
| UV OIL-SOL 311 | | | | | | | | x | x | | x | |
| UV OIL-SOL 312 | | | | | | | | x | x | | | x |
| UV OIL-SOL 313 | | | | | | | | x | | x | x | |
| UV OIL-SOL 314 | | | | | | | | x | | x | | x |
| UV OIL-SOL 315 | | | | | | | | x | | | x | x |
| UV OIL-SOL 316 | | | | | | | | | x | x | x | |
| UV OIL-SOL 317 | | | | | | | | | x | x | | x |
| UV OIL-SOL 318 | | | | | | | | | x | | x | x |
| UV OIL-SOL 319 | | | | | | | | | | x | x | x |
| 4-Filter combinations | | | | | | | | | | | | |
| UV OIL-SOL 320 | x | x | x | x | | | | | | | | |
| UV OIL-SOL 321 | x | x | x | | x | | | | | | | |
| UV OIL-SOL 322 | x | x | x | | | x | | | | | | |
| UV OIL-SOL 323 | x | x | x | | | | x | | | | | |
| UV OIL-SOL 324 | x | x | x | | | | | x | | | | |
| UV OIL-SOL 325 | x | x | x | | | | | | x | | | |
| UV OIL-SOL 326 | x | x | x | | | | | | | x | | |
| UV OIL-SOL 327 | x | x | x | | | | | | | | x | |
| UV OIL-SOL 328 | x | x | x | | | | | | | | | x |
| UV OIL-SOL 329 | x | x | | x | x | | | | | | | |
| UV OIL-SOL 330 | x | x | | x | | x | | | | | | |
| UV OIL-SOL 331 | x | x | | x | | | x | | | | | |
| UV OIL-SOL 332 | x | x | | x | | | | x | | | | |
| UV OIL-SOL 333 | x | x | | x | | | | | x | | | |
| UV OIL-SOL 334 | x | x | | x | | | | | | x | | |
| UV OIL-SOL 335 | x | x | | x | | | | | | | X | |
| UV OIL-SOL 336 | x | x | | x | | | | | | | | x |
| UV OIL-SOL 337 | x | x | | | x | x | | | | | | |
| UV OIL-SOL 338 | x | x | | | x | | x | | | | | |
| UV SOL 339 | x | x | | | x | | | x | | | | |
| UV OIL-SOL 340 | x | x | | | x | | | | x | | | |
| UV OIL-SOL 341 | x | x | | | x | | | | | x | | |
| UV OIL-SOL 342 | x | x | | | x | | | | | | x | |
| UV OIL-SOL 343 | x | x | | | x | | | | | | | x |
| UV OIL-SOL 344 | x | x | | | | x | X | | | | | |
| UV OIL-SOL 345 | x | x | | | | x | | x | | | | |
| UV OIL-SOL 346 | x | x | | | | x | | | x | | | |
| UV OIL-SOL 347 | x | x | | | | x | | | | x | | |
| UV OIL-SOL 348 | x | x | | | | x | | | | | x | |
| UV OIL-SOL 349 | x | x | | | | x | | | | | | x |
| UV OIL-SOL 350 | x | x | | | | | x | x | | | | |
| UV OIL-SOL 351 | x | x | | | | | x | | x | | | |
| UV OIL-SOL 352 | x | x | | | | | x | | | x | | |
| UV OIL-SOL 353 | x | x | | | | | x | | | | x | |
| UV OIL-SOL 354 | x | x | | | | | x | | | | | x |
| UV OIL-SOL 355 | x | x | | | | | | x | x | | | |
| UV OIL-SOL 356 | x | x | | | | | | x | | x | | |
| UV OIL-SOL 357 | x | x | | | | | | x | | | x | |
| UV OIL-SOL 358 | x | x | | | | | | x | | | | x |
| UV OIL-SOL 359 | x | x | | | | | | | x | x | | |
| UV OIL-SOL 360 | x | x | | | | | | | x | | x | |
| UV OIL-SOL 361 | x | x | | | | | | | x | | | x |
| UV OIL-SOL 362 | x | x | | | | | | | | x | x | |
| UV OIL-SOL 363 | x | x | | | | | | | | x | | x |
| UV OIL-SOL 364 | x | x | | | | | | | | | x | x |
| UV OIL-SOL 365 | x | | x | x | x | | | | | | | |
| UV OIL-SOL 366 | x | | x | x | | x | | | | | | |
| UV OIL-SOL 367 | x | | x | x | | | x | | | | | |

TABLE 2-continued

List of oil soluble organic UV-Filter-combinations

| | BP3 | BP4 | 3BC | BEMT | BMBM | DBT | DTS | EHT | MBC | EMC | BMP | DHHB |
|---|---|---|---|---|---|---|---|---|---|---|---|---|
| UV OIL-SOL 368 | x | | x | x | | | | x | | | | |
| UV OIL-SOL 369 | x | | x | x | | | | | x | | | |
| UV OIL-SOL 370 | x | | x | x | | | | | | x | | |
| UV OIL-SOL 371 | x | | x | x | | | | | | | x | |
| UV OIL-SOL 372 | x | | x | x | | | | | | | | x |
| UV OIL-SOL 373 | x | | x | | x | x | | | | | | |
| UV OIL-SOL 374 | x | | x | | x | | x | | | | | |
| UV OIL-SOL 375 | x | | x | | x | | | x | | | | |
| UV OIL-SOL 376 | x | | x | | x | | | | x | | | |
| UV OIL-SOL 377 | x | | x | | x | | | | | x | | |
| UV OIL-SOL 378 | x | | x | | x | | | | | | x | |
| UV OIL-SOL 379 | x | | x | | x | | | | | | | x |
| UV OIL-SOL 380 | x | | x | | | x | x | | | | | |
| UV OIL-SOL 381 | x | | x | | | x | | x | | | | |
| UV OIL-SOL 382 | x | | x | | | x | | | x | | | |
| UV OIL-SOL 383 | x | | x | | | x | | | | x | | |
| UV OIL-SOL 384 | x | | x | | | x | | | | | x | |
| UV OIL-SOL 385 | x | | x | | | x | | | | | | x |
| UV OIL-SOL 386 | x | | x | | | | x | x | | | | |
| UV OIL-SOL 387 | x | | x | | | | x | | x | | | |
| UV OIL-SOL 388 | x | | x | | | | x | | | x | | |
| UV OIL-SOL 389 | x | | x | | | | x | | | | x | |
| UV OIL-SOL 390 | x | | x | | | | x | | | | | x |
| UV OIL-SOL 391 | x | | x | | | | | x | x | | | |
| UV OIL-SOL 392 | x | | x | | | | | x | | x | | |
| UV OIL-SOL 393 | x | | x | | | | | x | | | x | |
| UV OIL-SOL 394 | x | | x | | | | | x | | | | x |
| UV OIL-SOL 395 | x | | x | | | | | | x | x | | |
| UV OIL-SOL 396 | x | | x | | | | | | x | | x | |
| UV OIL-SOL 397 | x | | x | | | | | | x | | | x |
| UV OIL-SOL 398 | x | | x | | | | | | | x | x | |
| UV OIL-SOL 399 | x | | x | | | | | | | x | | x |
| UV OIL-SOL 400 | x | | x | | | | | | | | x | x |
| UV OIL-SOL 401 | x | | | x | x | x | | | | | | |
| UV OIL-SOL 402 | x | | | x | x | | x | | | | | |
| UV OIL-SOL 403 | x | | | x | x | | | x | | | | |
| UV OIL-SOL 404 | x | | | x | x | | | | x | | | |
| UV OIL-SOL 405 | x | | | x | x | | | | | x | | |
| UV OIL-SOL 406 | x | | | x | x | | | | | | x | |
| UV OIL-SOL 407 | X | | | x | x | | | | | | | x |
| UV OIL-SOL 408 | x | | | x | | x | x | | | | | |
| UV OIL-SOL 409 | x | | | x | | x | | x | | | | |
| UV OIL-SOL 410 | x | | | x | | x | | | x | | | |
| UV OIL-SOL 411 | x | | | x | | x | | | | x | | |
| UV OIL-SOL 412 | x | | | x | | x | | | | | x | |
| UV OIL-SOL 413 | x | | | x | | x | | | | | | x |
| UV OIL-SOL 414 | x | | | x | | | x | x | | | | |
| UV OIL-SOL 415 | x | | | x | | | x | | x | | | |
| UV OIL-SOL 416 | x | | | x | | | x | | | x | | |
| UV OIL-SOL 417 | x | | | x | | | x | | | | x | |
| UV OIL-SOL 418 | x | | | x | | | x | | | | | x |
| UV OIL-SOL 419 | x | | | x | | | | x | x | | | |
| UV OIL-SOL 420 | x | | | x | | | | x | | x | | |
| UV OIL-SOL 421 | x | | | x | | | | x | | | x | |
| UV OIL-SOL 422 | x | | | x | | | | x | | | | x |
| UV OIL-SOL 423 | x | | | x | | | | | x | x | | |
| UV OIL-SOL 424 | x | | | x | | | | | x | | x | |
| UV OIL-SOL 425 | x | | | x | | | | | x | | | x |
| UV OIL-SOL 426 | x | | | x | | | | | | x | x | |
| UV OIL-SOL 427 | x | | | x | | | | | | x | | x |
| UV OIL-SOL 428 | x | | | x | | | | | | | x | x |
| UV OIL-SOL 429 | x | | | | x | x | x | | | | | |
| UV OIL-SOL 430 | x | | | | x | x | | x | | | | |
| UV OIL-SOL 431 | x | | | | x | x | | | x | | | |
| UV OIL-SOL 432 | x | | | | x | x | | | | x | | |
| UV OIL-SOL 433 | x | | | | x | x | | | | | x | |
| UV OIL-SOL 434 | x | | | | x | x | | | | | | x |
| UV OIL-SOL 435 | x | | | | x | | x | x | | | | |
| UV OIL-SOL 436 | x | | | | x | | x | | x | | | |
| UV OIL-SOL 437 | x | | | | x | | x | | | x | | |
| UV OIL-SOL 438 | x | | | | x | | x | | | | x | |
| UV OIL-SOL 439 | x | | | | x | | x | | | | | x |
| UV OIL-SOL 440 | x | | | | x | | | x | x | | | |
| UV OIL-SOL 441 | x | | | | x | | | x | | x | | |

TABLE 2-continued

List of oil soluble organic UV-Filter-combinations

| | Abbreviations | | | | | | | | | | | |
|---|---|---|---|---|---|---|---|---|---|---|---|---|
| | BP3 | BP4 | 3BC | BEMT | BMBM | DBT | DTS | EHT | MBC | EMC | BMP | DHHB |
| UV OIL-SOL 442 | x | | | | x | | | x | | | x | |
| UV OIL-SOL 443 | x | | | | x | | | x | | | | x |
| UV OIL-SOL 444 | x | | | | x | | | | x | x | | |
| UV OIL-SOL 445 | x | | | | x | | | | x | | x | |
| UV OIL-SOL 446 | x | | | | x | | | | x | | | x |
| UV OIL-SOL 447 | x | | | | x | | | | | x | x | |
| UV OIL-SOL 448 | x | | | | x | | | | | x | | x |
| UV OIL-SOL 449 | x | | | | x | | | | | | x | x |
| UV OIL-SOL 450 | x | | | | | x | x | x | | | | |
| UV OIL-SOL 451 | x | | | | | x | x | | x | | | |
| UV OIL-SOL 452 | x | | | | | x | x | | | x | | |
| UV OIL-SOL 453 | x | | | | | x | x | | | | x | |
| UV OIL-SOL 454 | x | | | | | x | x | | | | | x |
| UV OIL-SOL 455 | x | | | | | x | | x | x | | | |
| UV OIL-SOL 456 | x | | | | | x | | x | | x | | |
| UV OIL-SOL 457 | x | | | | | x | | x | | | x | |
| UV OIL-SOL 458 | x | | | | | x | | x | | | | x |
| UV OIL-SOL 459 | x | | | | | x | | | x | x | | |
| UV OIL-SOL 460 | x | | | | | x | | | x | | x | |
| UV OIL-SOL 461 | x | | | | | x | | | x | | | x |
| UV OIL-SOL 462 | x | | | | | x | | | | x | x | |
| UV OIL-SOL 463 | x | | | | | x | | | | x | | x |
| UV OIL-SOL 464 | x | | | | | x | | | | | x | x |
| UV OIL-SOL 465 | x | | | | | | x | x | x | | | |
| UV OIL-SOL 466 | x | | | | | | x | x | | x | | |
| UV OIL-SOL 467 | x | | | | | | x | x | | | x | |
| UV OIL-SOL 468 | x | | | | | | x | x | | | | x |
| UV OIL-SOL 469 | x | | | | | | x | | x | x | | |
| UV OIL-SOL 470 | x | | | | | | x | | x | | x | |
| UV OIL-SOL 471 | x | | | | | | x | | x | | | x |
| UV OIL-SOL 472 | x | | | | | | x | | | x | x | |
| UV OIL-SOL 473 | x | | | | | | x | | | x | | x |
| UV OIL-SOL 474 | x | | | | | | x | | | | x | x |
| UV OIL-SOL 475 | x | | | | | | | x | x | x | | |
| UV OIL-SOL 476 | x | | | | | | | x | x | | x | |
| UV OIL-SOL 477 | x | | | | | | | x | x | | | x |
| UV OIL-SOL 478 | x | | | | | | | x | | x | x | |
| UV OIL-SOL 479 | x | | | | | | | x | | x | | x |
| UV OIL-SOL 480 | x | | | | | | | x | | | x | x |
| UV OIL-SOL 481 | x | | | | | | | | x | x | x | |
| UV OIL-SOL 482 | x | | | | | | | | x | x | | x |
| UV OIL-SOL 483 | x | | | | | | | | x | | x | x |
| UV OIL-SOL 484 | x | | | | | | | | | x | x | x |
| UV OIL-SOL 485 | | x | x | x | x | | | | | | | |
| UV OIL-SOL 486 | | x | x | x | x | x | | | | | | |
| UV OIL-SOL 487 | | x | x | x | x | | x | | | | | |
| UV OIL-SOL 488 | | x | x | x | x | | | x | | | | |
| UV OIL-SOL 489 | | x | x | x | x | | | | x | | | |
| UV OIL-SOL 490 | | x | x | x | x | | | | | x | | |
| UV OIL-SOL 491 | | x | x | x | x | | | | | | x | |
| UV OIL-SOL 492 | | x | x | x | x | | | | | | | x |
| UV OIL-SOL 493 | | x | x | | x | x | | | | | | |
| UV OIL-SOL 494 | | x | x | | x | | x | | | | | |
| UV OIL-SOL 495 | | x | x | | x | | | x | | | | |
| UV OIL-SOL 496 | | x | x | | x | | | | x | | | |
| UV OIL-SOL 497 | | x | x | | x | | | | | x | | |
| UV OIL-SOL 498 | | x | x | | x | | | | | | x | |
| UV OIL-SOL 499 | | x | x | | x | | | | | | | x |
| UV OIL-SOL 490 | | x | x | | | x | x | | | | | |
| UV OIL-SOL 491 | | x | x | | | x | | x | | | | |
| UV OIL-SOL 492 | | x | x | | | x | | | x | | | |
| UV OIL-SOL 493 | | x | x | | | x | | | | x | | |
| UV OIL-SOL 494 | | x | x | | | x | | | | | x | |
| UV OIL-SOL 495 | | x | x | | | x | | | | | | x |
| UV OIL-SOL 496 | | x | x | | | | x | x | | | | |
| UV OIL-SOL 497 | | x | x | | | | x | | x | | | |
| UV OIL-SOL 498 | | x | x | | | | x | | | x | | |
| UV OIL-SOL 499 | | x | x | | | | x | | | | x | |
| UV OIL-SOL 500 | | x | x | | | | x | | | | | x |
| UV OIL-SOL 501 | | x | x | | | | | x | x | | | |
| UV OIL-SOL 502 | | x | x | | | | | x | | x | | |
| UV OIL-SOL 503 | | x | x | | | | | x | | | x | |
| UV OIL-SOL 504 | | x | x | | | | | x | | | | x |
| UV OIL-SOL 505 | | x | x | | | | | | x | x | | |

TABLE 2-continued

List of oil soluble organic UV-Filter-combinations

| | Abbreviations | | | | | | | | | | | |
|---|---|---|---|---|---|---|---|---|---|---|---|---|
| | BP3 | BP4 | 3BC | BEMT | BMBM | DBT | DTS | EHT | MBC | EMC | BMP | DHHB |
| UV OIL-SOL 506 | | x | x | | | | | | x | | x | |
| UV OIL-SOL 507 | | x | x | | | | | | x | | | x |
| UV OIL-SOL 508 | | x | x | | | | | | | x | x | |
| UV OIL-SOL 509 | | x | x | | | | | | | x | | x |
| UV OIL-SOL 510 | | x | x | | | | | | | | x | x |
| UV OIL-SOL 511 | | | x | x | x | x | | | | | | |
| UV OIL-SOL 512 | | | x | x | x | | x | | | | | |
| UV OIL-SOL 513 | | | x | x | x | | | x | | | | |
| UV OIL-SOL 514 | | | x | x | x | | | | x | | | |
| UV OIL-SOL 515 | | | x | x | x | | | | | x | | |
| UV OIL-SOL 516 | | | x | x | x | | | | | | x | |
| UV OIL-SOL 517 | | | x | x | x | | | | | | | x |
| UV OIL-SOL 518 | | | x | x | | x | x | | | | | |
| UV OIL-SOL 519 | | | x | x | | x | | x | | | | |
| UV OIL-SOL 520 | | | x | x | | x | | | x | | | |
| UV OIL-SOL 521 | | | x | x | | x | | | | x | | |
| UV OIL-SOL 522 | | | x | x | | x | | | | | x | |
| UV OIL-SOL 523 | | | x | x | | x | | | | | | x |
| UV OIL-SOL 524 | | | x | x | | | x | x | | | | |
| UV OIL-SOL 525 | | | x | x | | | x | | x | | | |
| UV OIL-SOL 526 | | | x | x | | | x | | | x | | |
| UV OIL-SOL 527 | | | x | x | | | x | | | | x | |
| UV OIL-SOL 528 | | | x | x | | | x | | | | | x |
| UV OIL-SOL 529 | | | x | x | | | | x | x | | | |
| UV OIL-SOL 530 | | | x | x | | | | x | | x | | |
| UV OIL-SOL 531 | | | x | x | | | | x | | | x | |
| UV OIL-SOL 532 | | | x | x | | | | x | | | | x |
| UV OIL-SOL 533 | | | x | x | | | | | x | x | | |
| UV OIL-SOL 534 | | | x | x | | | | | x | | x | |
| UV OIL-SOL 535 | | | x | x | | | | | x | | | x |
| UV OIL-SOL 536 | | | x | x | | | | | | x | x | |
| UV OIL-SOL 537 | | | x | x | | | | | | x | | x |
| UV OIL-SOL 538 | | | x | x | | | | | | | x | x |
| UV OIL-SOL 539 | | | | x | x | x | x | | | | | |
| UV OIL-SOL 540 | | | | x | x | x | | x | | | | |
| UV OIL-SOL 541 | | | | x | x | x | | | x | | | |
| UV OIL-SOL 542 | | | | x | x | x | | | | x | | |
| UV SOL 543 | | | | x | x | x | | | | | x | |
| UV OIL-SOL 544 | | | | x | x | x | | | | | | x |
| UV OIL-SOL 545 | | | | x | x | | x | x | | | | |
| UV OIL-SOL 546 | | | | x | x | | x | | x | | | |
| UV OIL-SOL 547 | | | | x | x | | x | | | x | | |
| UV OIL-SOL 548 | | | | x | x | | x | | | | x | |
| UV OIL-SOL 549 | | | | x | x | | x | | | | | x |
| UV OIL-SOL 550 | | | | x | x | | | x | x | | | |
| UV OIL-SOL 551 | | | | x | x | | | x | | x | | |
| UV OIL-SOL 552 | | | | x | x | | | x | | | x | |
| UV OIL-SOL 553 | | | | x | x | | | x | | | | x |
| UV OIL-SOL 554 | | | | x | x | | | | x | x | | |
| UV OIL-SOL 555 | | | | x | x | | | | x | | x | |
| UV OIL-SOL 556 | | | | x | x | | | | x | | | x |
| UV OIL-SOL 557 | | | | x | x | | | | | x | x | |
| UV OIL-SOL 558 | | | | x | x | | | | | x | | x |
| UV OIL-SOL 559 | | | | x | x | | | | | | x | x |
| UV OIL-SOL 560 | | | | | x | x | x | x | | | | |
| UV OIL-SOL 561 | | | | | x | x | x | | x | | | |
| UV OIL-SOL 562 | | | | | x | x | x | | | x | | |
| UV OIL-SOL 563 | | | | | x | x | x | | | | x | |
| UV OIL-SOL 564 | | | | | x | x | x | | | | | x |
| UV OIL-SOL 565 | | | | | x | x | | x | x | | | |
| UV OIL-SOL 566 | | | | | x | x | | x | | x | | |
| UV OIL-SOL 567 | | | | | x | x | | x | | | x | |
| UV OIL-SOL 568 | | | | | x | x | | x | | | | x |
| UV OIL-SOL 569 | | | | | x | x | | | x | x | | |
| UV OIL-SOL 570 | | | | | x | x | | | x | | x | |
| UV OIL-SOL 571 | | | | | x | x | | | x | | | x |
| UV OIL-SOL 572 | | | | | x | x | | | | x | x | |
| UV OIL-SOL 573 | | | | | x | x | | | | x | | x |
| UV OIL-SOL 574 | | | | | x | x | | | | | x | x |
| UV OIL-SOL 575 | | | | | x | | x | x | x | | | |
| UV OIL-SOL 576 | | | | | x | | x | x | | x | | |
| UV OIL-SOL 577 | | | | | x | | x | x | | | x | |
| UV OIL-SOL 578 | | | | | x | | x | x | | | | x |
| UV OIL-SOL 579 | | | | | x | | x | | x | x | | |

TABLE 2-continued

List of oil soluble organic UV-Filter-combinations

| | BP3 | BP4 | 3BC | BEMT | BMBM | DBT | DTS | EHT | MBC | EMC | BMP | DHHB |
|---|---|---|---|---|---|---|---|---|---|---|---|---|
| UV OIL-SOL 580 | | | | | | x | x | | x | | x | |
| UV OIL-SOL 581 | | | | | | x | x | | x | | | x |
| UV OIL-SOL 582 | | | | | | x | x | | | x | x | |
| UV OIL-SOL 583 | | | | | | x | x | | | x | | x |
| UV OIL-SOL 584 | | | | | | x | x | | | | x | x |
| UV OIL-SOL 585 | | | | | | x | | x | x | x | | |
| UV OIL-SOL 586 | | | | | | x | | x | x | | x | |
| UV OIL-SOL 587 | | | | | | x | | x | x | | | x |
| UV OIL-SOL 588 | | | | | | x | | x | | x | x | |
| UV OIL-SOL 589 | | | | | | x | | x | | x | | x |
| UV OIL-SOL 590 | | | | | | | | x | x | | x | x |
| UV OIL-SOL 591 | | | | | | | | x | x | x | x | |
| UV OIL-SOL 592 | | | | | | | | x | x | x | | x |
| UV OIL-SOL 593 | | | | | | | | x | x | | x | x |
| UV OIL-SOL 594 | | | | | | | | | x | x | x | x |

| Abbreviations | | |
|---|---|---|
| BP3 | Benzophenone 3 | 131-57-7 |
| BP4 | Benzophenone-4 | 4065-45-6 |
| 3BC | 3-Benzydilene Camphor | 15087-24-8 |
| BEMT | Bis-Ethylhexyloxyphenol Methoxyphenyl Triazine | 103597-45-1 |
| BMBM | Butyl Methoxydibenzoylmethane | 70356-09-1 |
| DBT | Diethylhexyl Butamido Triazone | 154702-15-5 |
| DTS | Drometrizole Trisiloxane | 155633-54-8 |
| EHT | Ethylhexyl Triazone | 88122-99-0 |
| MBC | Methylbenzylidencampher | |
| EMC | Ethylhexyl Methoxycinnamate | 36861-47-9 |
| BMP | Benzylidene malonate polysiloxane (BMP) | |
| DHHB | Diethylamino Hydroxy Benzoyl Hexyl Benzoate | |

Besides active ingredients, the core of the capsule according to the invention can also comprise hydrophobic auxiliaries such as oils or solvents which are usually used in the respective fields of application. In the case of cosmetic active ingredients, like the preferred UV filters, the organic active ingredient can be dissolved or suspended in typical oil components which are used in cosmetics.

Customary oil components in cosmetics are for example, paraffin oil, glyceryl stearate, isopropyl myristate, diisopropyl adipate, cetylstearyl 2-ethyihexanoate, hydrogenated polyisobutene, vaseline, caprylic/capric triglycerides, microcrystalline wax, lanolin and stearic acid. However, this list is exemplary and not exhaustive.

Particular preference is given to those sparingly water-soluble or water-insoluble organic active ingredients which are soluble or suspendable in the water-insoluble or sparingly water-soluble sol-gel precursor which is used for constructing the shell of the capsule according to the invention.

The present invention further provides cosmetic or pharmaceutical compositions, crop protection preparations, animal feeds, foods or nutritional supplements, comprising the capsules according to the invention having a core/shell structure which have been described above or which have been produced by the above-described method. Particular preference is given to cosmetics or pharmaceutical compositions for the area of skin protection against solar UV radiation (sun screens).

The cosmetic composition according to the present invention is especially useful for the protection of organic materials that are sensitive to ultraviolet light, especially human and animal skin and hair, against the action of UV radiation.

Such UV filter combinations are therefore suitable as light-protective agents in cosmetic, pharmaceutical and veterinary medicine preparations.

The cosmetic or pharmaceutical composition according to the present invention contains from 0.1 to 40% by weight, preferably from 0.1 to 15% by weight, especially preferred from 0.5 to 10% by weight, based on the total weight of the composition, of the microcapsule according to the present invention comprising the UV filter (o) in the core and a cosmetically tolerable adjuvant.

In addition to other properties, the cosmetic or pharmaceutical composition according to the present invention can be used as a radical scavenger by reducing significantly the number of UV-induced free radicals in skin when applied in a suitable cosmetic carrier.

The cosmetic composition may comprise in addition to the UV filter(s) (o) according to the present invention one or more further non-encapsulated UV filters. All the UV filters $(o_1)$-$(o_{20})$ may be used as non-encapsulated actives. Furthermore, water soluble UV filters, inorganic UV filters like titanium dioxide or zinc oxide or UV filters in micronized form which may be present in the cosmetic formulation as aqueous dispersions may be used.

Special preference is given to the light-protective agents indicated in the following Table 3:

TABLE 3

Suitable UV filter substances and adjuvants which can be additionally used with the UV absorber according to the present invention

| Chemical Name | CAS No. |
|---|---|
| Alpha-(2-oxoborn-3-ylidene)toluene-4-sulphonic acid and its salts (Mexoryl SL) | 56039-58-8 |
| Methyl N,N,N-trimethyl-4-[(4,7,7-trimethyl-3-oxobicyclo[2,2,1]hept-2-ylidene)methyl]anilinium sulphate (Mexoryl SO) | 52793-97-2 |
| 2-Propenamide, N-[[4-[(4,7,7-trimethyl-3-oxobicyclo[2.2.1]hept-2-ylidene)methyl]phenyl]methyl]-, homopolymer | 147897-12-9 |
| 3, 3'-(1,4-phenylenedimethylene)bis[7, 7-dimethyl-2-oxo-bicyclo[2.2.1]heptane-1 methanesulfonic acid] (Cibafast H) | 90457-82-2 |
| Zinc oxide (primary particle size 20-100 nm); for example Zinc oxide NDM, Zinc oxide Z-Cote HP1, Nanox Zinc oxide | 1314-13-2 |

TABLE 3-continued

Suitable UV filter substances and adjuvants which can be additionally used with the UV absorber according to the present invention

| Chemical Name | CAS No. |
|---|---|
| Phenol, 2-(2H-benzotriazol-2-yl)-4-methyl-6-[2-methyl-3-[1,3,3,3-tetramethyl-1-[(trimethylsilyl)oxy]disiloxanyl]propyl]-; drometrizole trisiloxane (Mexoryl XL) | 155633-54-8 |
| Dimethicodiethylbenzalmalonate; Polysilicone 15 (Parsol SLX) | 207574-74-1 |
| Benzenesulfonic acid, 3-(2H-benzotriazol-2-yl)-4-hydroxy-5-(1-methylpropyl)-, monosodium salt (Tinogard HS) | 92484-48-5 |
| 1-Dodecanarninium, N-[3-[[4-(dimethylamino)benzoyl]amino]-propyl]N,N-dimethyl-, salt with 4-methylbenzenesulfonic acid (1:1) (Escalol HP610) | 156679-41-3 |
| 1-Propanaminium, N,N,N-trimethyl-3-[(1-oxo-3-phenyl-2-propenyl)amino]-, chloride | 177190-98-6 |
| 1H-Benzimidazole-4,6-disulfonic acid, 2,2'-(1,4-phenylene)bis- | 70864-82-1 |
| 1,3,5-Triazine, 2,4,6-tris(4-methoxyphenyl)- | 7753-12-0 |
| 1,3,5-Triazine, 2,4,6-tris[4-[(2-ethylhexyl)oxy]phenyl]- | 208114-14-1 |
| 1-Propanaminium, 3-[[3-[3-(2H-benzotriazol-2-yl)-5-(1,1-dimethylethyl)-4-hydroxyphenyl]-1-oxopropyl]amino]-N,N-diethyl-N-methyl-, methyl sulfate (salt) | 340964-15-0 |
| 2-Propenoic acid, 3-(1H-imidazol-4-yl)- | 104-98-3 |
| Benzoic acid, 2-hydroxy-, [4-(1-methylethyl)phenyl]methyl ester | 94134-93-7 |
| 1,2,3-Propanetriol, 1-(4-aminobenzoate) (Glyceryl PABA) | 136-44-7 |
| Benzeneacetic acid, 3,4-dimethoxy-a-oxo- | 4732-70-1 |
| 2-Propenoic acid, 2-cyano-3,3-diphenyl-, ethyl ester | 5232-99-5 |
| Anthralinic acid, p-menth-3-yl ester | 134-09-8 |
| 2,2'-bis(1,4-phenylene)-1H-benzimidazole-4,6-disulphonic acid mono sodium salt or Disodium phenyl dibenzimidazole tetrasulfonate (Neo Heliopan AP) | 349580-12-7 |
| sterols (cholesterol, lanosterol, phytosterols), as described in WO0341675 | |
| mycosporines and/or mycosporine-like amino acids as described in WO2002039974, e.g. Helioguard 365 from Milbelle AG, isolated mycosporine like amino acids from the red alga porphyra umbilicalis (INCI: Porphyra Umbilicalis) that are encapsulated into liposomes) | |
| alpha-lipoic-acid as described in DE 10229995 | |
| synthetic organic polymers as described in EP 1 371 358, [0033]-[0041] | |
| phyllosilicates as described in EP 1371357 [0034]-[0037] | |
| silica compounds as described in EP1371356, [0033]-[0041] | |
| inorganic particles as described in DE10138496 [0043]-[0055] | |
| latex particles as described in DE10138496 [0027]-[0040] | |
| 1H-Benzimidazole-4,6-disulfonic acid, 2,2'-(1,4-phenylene)bis-, disodium salt; Bisimidazylate (Neo Heliopan APC) | 180898-37-7 |
| Di-2-ethylhexyl-3,5-dimethoxy-4-hydroxy-benzalmalonate (Oxynex ST, EMD Chemicals, as described in US 20040247536) | |
| Z-COTE ® MAX: Zinc Oxide (and) Diphenyl Capryl Methicone | |
| Z-COTE HP1: Zinc Oxide (and) Triethoxycaprylylsilane | |
| 1,3,5-Triazine-2,4,6-triamine, N2,N4-bis[4-[5-(1,1-dimethylpropyl)-2-benzoxazolyl]phenyl]-N6-(2-ethylhexyl)- (Uvasorb K2A) | 288254-16-0 |
| 1,1-[(2,2'-Dimethylpropoxy)carbonyl]-4,4-diphenyl-1,3-butadiene | 363602-15-7 |

If the cosmetic compositions according to the present invention represent water- and oil-containing emulsions (e.g. W/O, O/W, O/W/O and W/O/W emulsions or microemulsions) they contain, for example, from 0.1 to 30% by weight, preferably from 0.1 to 15% by weight and especially from 0.5 to 10% by weight, based on the total weight of the composition, of the microcapsule according to the present invention, from 1 to 60% by weight, especially from 5 to 50% by weight and preferably from 10 to 35% by weight, based on the total weight of the composition, of at least one oil component, from 0 to 30% by weight, especially from 1 to 30% by weight and preferably from 4 to 20% by weight, based on the total weight of the composition, of at least one emulsifier, from 10 to 90% by weight, especially from 30 to 90% by weight, based on the total weight of the composition, of water, and from 0 to 88.9% by weight, especially from 1 to 50% by weight, of further cosmetically tolerable adjuvants.

Suitable oil components of oil-containing compositions (e.g. oils, W/O, O/W, O/W/O and W/O/W emulsions or microemulsions) are for example Guerbet alcohols based on fatty alcohols having from 6 to 18, preferably from 8 to 10, carbon atoms, esters of linear $C_6$-$C_{24}$ fatty acids with linear $C_3$-$C_{24}$ alcohols, esters of branched $C_6$-$C_{13}$ carboxylic acids with linear $C_6$-$C_{24}$ fatty alcohols, esters of linear $C_6$-$C_{24}$ fatty acids with branched alcohols, especially 2-ethylhexanol, esters of hydroxycarboxylic acids with linear or branched $C_6$-$C_{22}$ fatty alcohols, especially dioctyl malates, esters of linear and/or branched fatty acids with polyhydric alcohols (for example propylene glycol, dimer diol or trimer triol) and/or Guerbet alcohols, triglycerides based on $C_6$-$C_{10}$ fatty acids, liquid mono-/di-/tri-glyceride mixtures based on $C_6$-$C_{18}$ fatty acids, esters of $C_6$-$C_{24}$ fatty alcohols and/or Guerbet alcohols with aromatic carboxylic acids, especially benzoic acid, esters of $C_2$-$C_{12}$ dicarboxylic acids with linear or branched alcohols having from 1 to 22 carbon atoms or polyols having from 2 to 10 carbon atoms and from 2 to 6 hydroxy groups, vegetable oils (such as sunflower oil, olive oil, soybean oil, rapeseed oil, almond oil, jojoba oil, orange oil, wheat germ oil, peach kernel oil and the liquid components of coconut oil), branched primary alcohols, substituted cyclohexanes, linear and branched $C_6$-$C_{22}$ fatty alcohol carbonates, Guerbet carbonates, esters of benzoic acid with linear and/or branched $C_6$-$C_{22}$ alcohols (e.g. Finsolv® TN), linear or branched, symmetric or asymmetric dialkyl ethers having a total of from 12 to 36 carbon atoms, especially from 12 to 24 carbon atoms, for example di-n-octyl ether, di-n-decyl ether, di-n-nonyl ether, di-n-undecyl ether, di-n-dodecyl ether, n-hexyl n-octyl ether, n-octyl n-decyl ether, n-decyl n-undecyl ether, n-undecyl n-dodecyl ether, n-hexyl n-undecyl ether, di-tert-butyl ether, diisopentyl ether, di-3-ethyldecyl ether, tert-butyl n-octyl ether, isopentyl n-octyl ether and 2-methyl pentyl-n-octyl ether; ring-opening products of epoxidised fatty acid esters with polyols, silicone oils and/or aliphatic or naphthenic hydrocarbons. Also of importance are monoesters of fatty acids with alcohols having from 3 to 24 carbon atoms. That group of substances comprises the esterification products of fatty acids having from 8 to 24 carbon atoms, for example ca-caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselinic acid, linoleic acid, linolenic acid, elaeostearic acid, arachidic acid, gadoleic acid, behenic acid and erucic acid and technical-grade mixtures thereof (obtained, for example, in the pressure removal of natural fats and oils, in the reduction of aldehydes from Roelen's oxosynthesis or in the dimerisation of unsaturated fatty acids) with alcohols, for example isopropyl alcohol, caproic alcohol, capryl alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linoyl alcohol, linolenyl alcohol, elaeostearyl alcohol, arachidyl alcohol, gadoleyl alcohol, behenyl alcohol, erucyl alcohol and brassidyl alcohol and technical-grade mixtures thereof (obtained, for example, in the high-pressure hydrogenation of technical-grade methyl esters based on fats and oils or aldehydes from Roelen's oxosynthesis and as monomer fractions in the dimerisation of unsaturated fatty alcohols). Of special importance are isopropyl myristate, isono-nanoic acid $C_{16}$-$C_{18}$alkyl esters, stearic acid 2-ethylhexyl ester, cetyl oleate, glycerol tricaprylate, coconut fatty alcohol caprinate/caprylate and n-butyl stearate. Further oil components that can be used are dicarboxylic acid esters, such as di-n-butyl adipate, di(2-ethylhexyl) adipate, di(2-ethylhexyl) succinate and diisotridecyl acetate, and also diol esters, such as ethylene glycol dioleate, ethylene glycol diisotridecanoate, propylene glycol di(2-ethylhexanoate), propylene glycol diisostearate, propylene glycol dipelargonate, butanediol diisostearate and neopentyl glycol dicaprylate. Preferred mono- or poly-ols are ethanol, isopropanol, propylene glycol, hexylene glycol, glycerol and sorbitol. It is also possible to use di- and/or trivalent metal salts (alkaline earth metal, $Al^{3+}$ inter alia) of one or more alkyl carboxylic acids.

The oil components can be used in an amount of, for example, from 1 to 60% by weight, especially from 5 to 50% by weight and preferably from 10 to 35% by weight, based on the total weight of the composition.

Any conventionally usable emulsifier can be used for the cosmetic compositions according to the present invention.

Suitable emulsifiers are for example, non-ionic surfactants from the following groups:
  addition products of from 2 to 30 mol of ethylene oxide and/or from 0 to 5 mol of propylene oxide with linear fatty alcohols having from 8 to 22 carbon atoms, with fatty acids having from 12 to 22 carbon atoms and with alkylphenols having from 8 to 15 carbon atoms in the alkyl group, for example ceteareth-20 or ceteareth-12;
  $C_{12}$-$C_{22}$ fatty acid mono- and di-esters of addition products of from 1 to 30 mol of ethylene oxide with polyols having from 3 to 6 carbon atoms, especially with glycerol;
  glycerol mono- and di-esters and sorbitan mono- and di-esters of saturated and unsaturated fatty acids having from 6 to 22 carbon atoms and ethylene oxide addition products thereof, for example glyceryl stearates, glyceryl isostearates, glyceryl oleates, sorbitan oleates or sorbitan sesquioleates;
  $C_8$-$C_{22}$alkyl-mono- and -oligo-glycosides and ethoxylated analogues thereof, degrees of oligomerisation of from 1.1 to 5, especially from 1.2 to 1.4, being preferred, and glucose being preferred as the sugar component;
  addition products of from 2 to 60 mol, especially from 15 to 60 mol, of ethylene oxide with castor oil and/or hydrogenated castor oil;
  polyol esters and especially polyglycerol esters, for example diisostearoyl polyglyceryl-3-diisostearates, polyglyceryl-3-diisostearates, triglyceryl diisostearates, polyglyceryl-2-sesquiisostearates or polyglyceryl dimerates. Mixtures of compounds from a plurality of those substance classes are also suitable;
  partial esters based on linear, branched, unsaturated or saturated $C_6$-$C_{22}$ fatty acids, ricinoleic acid and also 12-hydroxystearic acid and on glycerol, polyglycerol, pentaerythritol, dipentaerythritol, sugar alcohols (e.g. sorbitol), alkyl glucosides (e.g. methyl glucoside, butyl glucoside, lauryl glucoside) and also polyglucosides (e.g. cellulose), for example polyglyceryl-2-dihydroxystearates or polyglyceryl-2-diricinoleates;
  mono-, di- and tri-alkyl phosphates and also mono-, di- and/or tri-PEG-alkyl phosphates and salts thereof;
  wool wax alcohols;
  one or more ethoxylated esters of natural derivatives, for example polyethoxylated esters of hydrogenated castor oil;
  silicone oil emulsifiers, for example silicone polyol;
  polysiloxane/polyalkyl/polyether copolymers and corresponding derivatives, for example cetyl dimethicone copolyol;
  mixed esters of pentaerythritol, fatty acids, citric acid and fatty alcohol (see DE-A-1 165 574) and/or mixed esters of fatty acids having from 6 to 22 carbon atoms, methylglucose and polyols, preferably glycerol or polyglycerol, for example polyglyceryl-3-glucose distearates, polyglyceryl-3-glucose dioleates, methyl gluglucose dioleates or dicocoyl pentaerythryl distearyl citrates; and also
  polyalkylene glycols.

The addition products of ethylene oxide and/or of propylene oxide with fatty alcohols, fatty acids, alkylphenols, glycerol mono- and di-esters and also sorbitan mono- and di-esters of fatty acids, or with castor oil, are known, commercially available products. They are usually homologue mixtures, the average degree of alkoxylation of which corresponds to the ratio of the amounts of ethylene oxide and/or propylene oxide and substrate with which the addition reaction is carried out. $C_{12}$-$C_{18}$ fatty acid mono- and di-esters of addition products of ethylene oxide with glycerol are known, for example, from DE-A-2 024 051 as fat-restoring substances for cosmetic preparations.

$C_8$-$C_{18}$Alkyl-mono- and -oligo-glycosides, their preparation and their use are known from the prior art. They are prepared especially by reacting glucose or oligosaccharides with primary alcohols having from 8 to 18 carbon atoms. Suitable glycoside radicals include monoglycosides in which a cyclic sugar radical is glycosidically bonded to the fatty alcohol and also oligomeric glycosides having a degree of oligomerisation of up to preferably about 8. The degree of oligomerisation is a statistical average value based on a homologue distribution customary for such technical-grade products.

It is also possible to use zwitterionic surfactants as emulsifiers. The term "zwitterionic surfactants" denotes especially surface-active compounds that carry at least one quaternary ammonium group and at least one carboxylate and/or sulfonate group in the molecule. Zwitterionic surfactants that are especially suitable are the so-called betaines, such as N-alkyl-N,N-dimethylammonium glycinates, for example cocoalkyl-dime-thylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazolines each having from 8 to 18 carbon atoms in the alkyl or acyl group and also cocoacylaminoethylhydroxyethylcarboxymethylglycinate. Special preference is given to the fatty acid amide derivative known by the CTFA name cocamidopropyl betaine. Likewise suitable as emulsifiers are ampholytic surfactants. Ampholytic surfactants are to be understood as meaning especially those which, in addition to containing a $C_8$-$C_{18}$-alkyl or -acyl group, contain at least one free amino group and at least one —COOH or —$SO_3H$ group in the molecule and are capable of forming internal salts. Examples of suitable ampholytic surfactants include N-alkylglycines, N-alkylpropi-onic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids, each having approximately from 8 to 18 carbon atoms in the alkyl group.

Ampholytic surfactants to which special preference is given are N-cocoalkylaminopropionate, cocoacylaminoethylaminopropionate and $C_{12}$-$C_{18}$acylsarcosine. In addition to the ampholytic emulsifiers there also come into consideration quaternary emulsifiers, special preference is given to those of the esterquat type, preferably methyl-quaternised di-fatty acid triethanolamine ester salts.

Non-ionic emulsifiers are preferred, preferably ethoxylated fatty alcohols having from 8 to 22 carbon atoms and from 4 to 30 EO units.

The emulsifiers may be used in an amount of, for example, from 1 to 30% by weight, especially from 4 to 20% by weight and preferably from 5 to 10% by weight, based on the total weight of the composition. It is, however, also possible in principle to dispense with the use of emulsifiers.

The compositions according to the invention, for example creams, gels, lotions, alcoholic and aqueous/alcoholic solutions, emulsions, wax/fat compositions, stick preparations, powders or ointments, may in addition contain, as further adjuvants and additives, mild surfactants, super-fatting agents, pearlescent waxes, consistency regulators, thickeners, polymers, silicone compounds, fats, waxes, stabilisers, biogenic active ingredients, deodorising active ingredients, anti-dandruff agents, film formers, swelling agents, antioxidants, hydrotropic agents, preservatives, insect repellents, self-tanning agents, solubilizers, perfume oils, colorants, bacteria-inhibiting agents and the like.

Substances suitable for use as super-fatting agents are, for example, lanolin and lecithin and also polyethoxylated or acrylated lanolin and lecithin derivatives, polyol fatty acid esters, monoglycerides and fatty acid alkanolamides, the latter simultaneously acting as foam stabilisers.

Examples of suitable mild surfactants, that is to say surfactants especially well tolerated by the skin, include fatty alcohol polyglycol ether sulfates, monoglyceride sulfates, mono- and/or di-alkyl sulfosuccinates, fatty acid isethionates, fatty acid sarcosinates, fatty acid taurides, fatty acid glutamates, α-olefin sulfonates, ether carboxylic acids, alkyl oligoglucosides, fatty acid glucamides, alkylamidobetaines and/or protein fatty acid condensation products, the latter preferably being based on wheat proteins.

Suitable pearlescent are for example: alkylene glycol esters, especially ethylene glycol distearate; fatty acid alkanolamides, especially coco fatty acid diethanolamide; partial glycerides, especially stearic acid monoglyceride; esters of polyvalent, unsubstituted or hydroxy-substituted carboxylic acids with fatty alcohols having from 6 to 22 carbon atoms, especially long-chained esters of tartaric acid; fatty substances, for example fatty alcohols, fatty ketones, fatty aldehydes, fatty ethers and fatty carbonates, which in total have at least 24 carbon atoms, especially laurone and distearyl ether; fatty acids, such as stearic acid, hydroxystearic acid or behenic acid, ring-opening products of olefin epoxides having from 12 to 22 carbon atoms with fatty alcohols having from 12 to 22 carbon atoms and/or polyols having from 2 to 15 carbon atoms and from 2 to 10 hydroxy groups, and mixtures thereof.

Suitable consistency regulators are especially fatty alcohols or hydroxy fatty alcohols having from 12 to 22 carbon atoms and preferably from 16 to 18 carbon atoms, and in addition partial glycerides, fatty acids and hydroxy fatty acids. Preference is given to a combination of such substances with alkyl-oligoglucosides and/or fatty acid N-methylglucamides of identical chain length and/or polyglycerol poly-12-hydroxystearates. Suitable thickeners include, for example, Aerosil types (hydrophilic silicic acids), polysaccharides, especially xanthan gum, guar-guar, agar-agar, alginates and Tyloses, carboxymethyl cellulose and hydroxymethyl cellulose, also relatively high molecular weight polyethylene glycol mono- and di-esters of fatty acids, polyacrylates (e.g. Carbopol® from Goodrich or Synthalen® from Sigma), polyacrylamides, polyvinyl alcohol and polyvinylpyrrolidone, surfactants, for example ethoxylated fatty acid glycerides, esters of fatty acids with polyols, for example pentaerythritol or trimethylolpropane, fatty alcohol ethoxylates with restricted homologue distribution and alkyl-oligoglucosides as well as electrolytes, such as sodium chloride or ammonium chloride.

Suitable cationic polymers are, for example, cationic cellulose derivatives, for example a quaternised hydroxymethyl cellulose obtainable under the name Polymer JR 400® from Amerchol, cationic starch, copolymers of diallylammonium salts and acrylamides, quaternised vinylpyrrolidone/vinyl imidazole polymers, for example Luviquat® (BASF), condensation products of polyglycols and amines, quaternised collagen polypeptides, for example lauryldimonium hydroxypropyl hydrolyzed collagen (Lamequat® L/Grünau), quaternised wheat polypeptides, polyethyleneimine, cationic silicone polymers, for example amidomethicones, copolymers of adipic acid and dimethylaminohydroxypropyldiethylenetriamine (Cartaretin®/Sandoz), copolymers of acrylic acid with dimethyldiallylammonium chloride (Merquat® 550/Chemviron), polyaminopolyamides, as described, for example, in FR-A-2 252 840, and the crosslinked water-soluble polymers thereof, cationic chitin derivatives, for example quaternised chitosan, optionally distributed as microcrystals; condensation products of dihaloalkyls, for example dibromobutane, with bisdialkylamines, for example bisdimethylamino-1,3-propane, cationic guar gum, for example Jaguar® C-17, Jaguar® C-16 from Celanese, quaternised ammonium salt polymers, for example Mirapol® A-15, Mirapol® AD-1, Mirapol® AZ-1 from Miranol.

Suitable anionic, zwitterionic, amphoteric and non-ionic polymers are for example, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and esters thereof, uncrosslinked polyacrylic acids and polyacrylic acids crosslinked with polyols, acrylamidopropyltrimethylammonium chloride/acrylate copolymers, octyl acrylamide/methyl methacrylate/tert-butylaminoethyl methacrylate/2-hydroxypropyl methacrylate copolymers, polyvinyl pyrrolidone, vinylpyrrolidone/vinyl acetate copolymers, vinylpyrrolidone/dimethylaminoethyl methacrylate/vinyl caprolactam terpolymers and also optionally derivatised cellulose ethers and silicones.

Suitable silicone compounds are, for example, dimethylpolysiloxanes, methylphenyl-polysiloxanes, cyclic silicones, and also amino-, fatty acid-, alcohol-, polyether-, epoxy-, fluorine-, glycoside- and/or alkyl-modified silicone compounds, which at room temperature may be in either liquid or resinous form. Also suitable are simethicones, which are mixtures of dimethicones having an average chain length of from 200 to 300 dimethylsiloxane units with hydrogenated silicates. A detailed survey by Todd et al. of suitable volatile silicones may in addition be found in Cosm. Toil. 91, 27 (1976).

Typical examples of fats are glycerides, and as waxes there come into consideration, inter alia, beeswax, carnauba wax, candelilla wax, montan wax, paraffin wax, hydrogenated castor oils and fatty acid esters or microwaxes solid at room temperature option-optionally in combination with hydrophilic waxes, e.g. cetylstearyl alcohol or partial glycerides. Metal salts of fatty acids, for example magnesium, aluminium and/or zinc stearate or ricinoleate, may be used as stabilizers.

Biogenic active ingredients are to be understood as meaning, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts and vitamin complexes.

Suitable deodorizing active ingredients are for example, antiperspirants like aluminium chlorohydrates (see J. Soc. Cosm. Chem. 24, 281 (1973)). Aluminium chlorohydrate corresponding to formula $Al_2(OH)_5Cl \times 2.5\ H_2O$, known and commercially available under the trade mark Locron® of Hoechst AG, Frankfurt (FRG), is especially preferred (see J. Pharm. Pharmacol. 26, 531 (1975)). Beside the chlorohydrates, it is also possible to use aluminium hydroxy-acetates and acidic aluminium/zirconium salts. Esterase inhibitors may be added as further deodorising active ingredients. Such inhibitors are preferably trialkyl citrates, such as trimethyl citrate, tripropyl citrate, triisopropyl citrate, tributyl citrate and especially triethyl citrate (Hydagen® CAT, Henkel KGaA, Düsseldorf/FRG), which inhibit enzyme activity and hence reduce odour formation. Further suitable esterase inhibitors are sterol sulfates or phosphates, for example lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester and hydroxycarboxylic acids and esters thereof, for example citric acid, malic acid, tartaric acid or tartaric acid diethyl ester. Antibacterial active ingredients that influence the microbial flora and kill, or inhibit the growth of, sweat-decomposing bacteria can likewise be present in the preparations (especially in stick preparations). Examples include chitosan, phenoxyethanol and chlorhexidine gluconate. 5-Chloro-2-(2,4-dichlorophenoxy)-phenol (Irgasan®, BASF) has also proved especially effective.

Suitable anti-dandruff agents are for example, climbazole, octopirox and zinc pyrithione.

Customary film formers include, for example, chitosan, microcrystalline chitosan, quaternised chitosan, polyvinylpyrrolidone, vinylpyrrolidone/vinyl acetate copolymers, polymers of quaternary cellulose derivatives containing a high proportion of acrylic acid, collagen, hyaluronic acid and salts thereof and similar compounds. Suitable swelling agents for aqueous phases are montmorillonites, clay mineral substances, Pemulen and also alkyl-modified types of Carbopol (Goodrich). Further suitable polymers and swelling agents can be found in the review by R. Lochhead in Cosm. Toil. 108, 95 (1993).

In addition to the primary light-protective substances it is also possible to use secondary light-protective substances of the antioxidant type which interrupt the photochemical reaction chain triggered when UV radiation penetrates the skin or hair. Typical examples of such antioxidants are amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotenoids, carotenes (e.g. α-carotene, β-carotene, lycopene) and derivatives thereof, chlorogenic acid and derivatives thereof, lipoic acid and derivatives thereof (e.g. dihydrolipoic acid), aurothioglycose, propylthiouracil and other thiols (e.g. thioredoxin, glutathione, cysteine, cystine, cystamine and the glycosyl, N-acetyl, methyl, ethyl, propyl, amyl, butyl, lauryl, palmitoyl, oleyl, γ-linoleyl, cholesteryl and glyceryl esters thereof) and also salts thereof, dilauryl thiodipropionate, distearyl thiodipropionate, thiodipropionic acid and derivatives thereof (esters, ethers, peptides, lipids, nucleotides, nucleosides and salts) and also sulfoximine compounds (e.g. buthionine sulfoximines, homocysteine sulfoximine, buthionine sulfones, penta-, hexa-, hepta-thionine sulfoximine) in very small tolerable amounts (e.g. from pmol to μmol/kg), also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, magnesium ascorbyl phosphate, ascorbyl acetate), tocopherols and derivatives (e.g. vitamin E acetate), vitamin A and derivatives (e.g. vitamin A palmitate) and also coniferyl benzoate of benzoin resin, rutinic acid and derivatives thereof, α-glycosylrutin, ferulic acid, furfurylidene glucitol, carnosine, butyl hydroxytoluene, butyl hydroxyanisole, resinous nordihydroguaiaretic acid, nordihydroguaiaretic acid, trihydroxybutyrophenone, uric acid and derivatives thereof, mannose and derivatives thereof, superoxide dismutase, N-[3-(3,5-di-tert-butyl-4-hydroxyphenyl)propionyl]sulfanilic acid (and salts thereof, for example the sodium salts), zinc and derivatives thereof (e.g. ZnO, $ZnSO_4$), selenium and derivatives thereof (e.g. selenium methio-nine), stilbene and derivatives thereof (e.g. stilbene oxide, trans-stilbene oxide) and the derivatives suitable according to the invention (salts, esters, ethers, sugars, nucleotides, nucleosides, peptides and lipids) of those mentioned active ingredients. HALS(="Hindered Amine Light Stabilizers") compounds may also be mentioned. The amount of antioxidants present is usually from 0.001 to 30% by weight, preferably from 0.01 to 3% by weight, based on the weight of the cosmetic composition according to the present invention.

For improvement of the flow behavior it is also possible to employ hydrotropic agents, for example ethanol, isopropyl alcohol or polyols. Suitable polyols for that purpose comprise preferably from 2 to 15 carbon atoms and at least two hydroxy groups.

The polyols may also contain further functional groups, especially amino groups, and/or may be modified with nitrogen. Typical examples are as follows:
glycerol;
alkylene glycols, for example ethylene glycol, diethylene glycol, propylene glycol, butylene glycol, hexylene glycol and also polyethylene glycols having an average molecular weight of from 100 to 1000 Dalton;
technical oligoglycerol mixtures having an intrinsic degree of condensation of from 1.5 to 10, for example technical diglycerol mixtures having a diglycerol content of from 40 to 50% by weight;
methylol compounds, such as, especially, trimethylolethane, trimethylolpropane, trimethylolbutane, pentaerythritol and dipentaerythritol;
lower alkyl-glucosides, especially those having from 1 to 8 carbon atoms in the alkyl radical, for example methyl and butyl glucoside;
sugar alcohols having from 5 to 12 carbon atoms, for example sorbitol or mannitol;
sugars having from 5 to 12 carbon atoms, for example glucose or saccharose;
amino sugars, for example glucamine;

dialcohol amines, such as diethanolamine or 2-amino-1, 3-propanediol.

Suitable preservatives include, for example, phenoxyethanol, formaldehyde solution, Parabens, pentandiol or sorbic acid and the further substance classes listed in Schedule 6, Parts A and B of the Cosmetics Regulations.

Suitable perfume oils are mixtures of natural and/or synthetic aromatic substances. Representatives of natural aromatic substances are, for example, extracts from blossom (lilies, lavender, roses, jasmine, neroli, ylang-ylang), from stems and leaves (geranium, patchouli, petitgrain), from fruit (aniseed, coriander, carraway, juniper), from fruit peel (bergamot, lemons, oranges), from roots (mace, angelica, celery, cardamom, costus, iris, calmus), from wood (pinewood, sandalwood, guaiacum wood, cedarwood, rosewood), from herbs and grasses (tarragon, lemon grass, sage, thyme), from needles and twigs (spruce, pine, Scots pine, mountain pine), from resins and balsams (galbanum, elemi, benzoin, myrrh, olibanum, opoponax). Animal raw materials also come into consideration, for example civet and castoreum. Typical synthetic aromatic substances are, for example, products of the ester, ether, aldehyde, ketone, alcohol or hydrocarbon type.

Aromatic substance compounds of the ester type are, for example, benzyl acetate, phenoxy-ethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allylcyclohexyl propionate, styrallyl propionate and benzyl salicylate. The ethers include, for example, benzyl ethyl ether; the aldehydes include, for example, the linear alkanals having from 8 to 18 hydrocarbon atoms, citral, citronellal, citronellyl oxyacetaldehyde, cyclamen aldehyde, hydroxycitronellal, lilial and bourgeonal; the ketones include, for example, the ionones, α-isomethylionone and methyl cedryl ketone; the alcohols include, for example, anethol, citronellol, eugenol, isoeugenol, geraniol, linalool, phenyl ethyl alcohol and terpinol; and the hydrocarbons include mainly the terpenes and balsams. It is preferable, however, to use mixtures of various aromatic substances that together produce an attractive scent. Ethereal oils of relatively low volatility, which are chiefly used as aroma components, are also suitable as perfume oils, e.g. sage oil, camomile oil, clove oil, melissa oil, oil of cinnamon leaves, lime blossom oil, juniper berry oil, vetiver oil, olibanum oil, galbanum oil, labolanum oil and lavandin oil. Preference is given to the use of bergamot oil, dihydromyrcenol, lilial, lyral, citronellol, phenyl ethyl alcohol, α-hexyl cinnamaldehyde, geraniol, benzyl acetone, cyclamen aldehyde, linalool, boisambrene forte, ambroxan, indole, hedione, sandelice, lemon oil, tangerine oil, orange oil, allyl amyl glycolate, cyclovertal, lavandin oil, muscatel sage oil, β-damascone, bourbon geranium oil, cyclohexyl salicylate, vertofix coeur, iso-E-Super, Fixolide NP, evernyl, iraldein gamma, phenylacetic acid, geranyl acetate, benzyl acetate, rose oxide, romillat, irotyl and floramat alone or in admixture with one another.

As colorants the substances that are suitable and permitted for cosmetic purposes, as compiled, for example, in the publication "Kosmetische Färbemittel" of the Farbstoffkommission der Deutschen Forschungsgemeinschaft, Verlag Chemie, Wein-Weinheim, 1984, pages 81 to 106 may be used. The colorants are usually used in concentrations of from 0.001 to 0.1% by weight, based on the total mixture.

Typical examples of bacteria-inhibiting agents are preservatives that have a specific action against gram-positive bacteria, such as 2,4,4'-trichloro-2'-hydroxydiphenyl ether, chlorhexidine (1,6-di(4-chlorophenyl-biguanido)hexane) or TCC (3,4,4'-trichlorocarbanilide).

A large number of aromatic substances and ethereal oils also have antimicrobial properties. Typical examples are the active ingredients eugenol, menthol and thymol in clove oil, mint oil and thyme oil. A natural deodorizing agent of interest is the terpene alcohol farnesol (3,7,11-trimethyl-2, 6,10-dodecatrien-1-ol), which is present in lime blossom oil. Glycerol monolaurate has also proved to be a bacteriostatic agent. The amount of the additional bacteria-inhibiting agents present is usually from 0.1 to 2% by weight, based on the solids content of the cosmetic composition according to the present invention.

The cosmetic compositions according to the present invention may furthermore contain as adjuvants anti-foams, such as silicones, structurants, such as maleic acid, solubilizers, such as ethylene glycol, propylene glycol, glycerol or diethylene glycol, opacifi-ers, such as latex, styrene/PVP or styrene/acrylamide copolymers, complexing agents, such as EDTA, NTA, β-alaninediacetic acid or phosphonic acids, propellants, such as propane/butane mixtures, $N_2O$, dimethyl ether, $CO_2$, $N_2$ or air, so-called coupler and developer components as oxidation dye precursors, thioglycolic acid and derivatives thereof, thiolactic acid, cysteamine, thiomalic acid or α-mercaptoethanesulfonic acid as reducing agents or hydrogen peroxide, potassium bromate or sodium bromate as oxidizing agent.

Insect repellents are for example, N,N-diethyl-m-toluamide, 1,2-pentanediol or insect repellent 3535.

Suitable self-tanning agents are dihydroxyacetone, erythrulose or mixtures of dihydroxyacetone and erythrulose.

Cosmetic formulations according to the invention are contained in a wide variety of cosmetic preparations, especially the following preparations:

skin-care preparations, e.g. skin-washing and cleansing preparations in the form of tablet-form or liquid soaps, synthetic detergents or washing pastes, bath preparations, e.g. liquid (foam baths, milks, shower preparations) or solid bath preparations, e.g. bath cubes and bath salts;

skin-care preparations, e.g. skin emulsions, multi-emulsions or skin oils;

cosmetic personal care preparations, e.g. facial make-up in the form of day creams or powder creams, face powder (loose or pressed), rouge or cream make-up, eye-care preparations, e.g. eye shadow preparations, mascara, eyeliner, eye creams or eye-fix creams; lip-care preparations, e.g. lipsticks, lip gloss, lip contour pencils, nail-care preparations, such as nail varnish, nail varnish removers, nail hardeners or cuticle removers;

foot-care preparations, e.g. foot baths, foot powders, foot creams or foot balsams, special deodorants and antiperspirants or callus-removing preparations;

light-protective preparations, such as sun milks, lotions, creams or oils, sunblocks or tropicals, pre-tanning preparations or after-sun preparations; skin-tanning preparations, e.g. self-tanning creams;

depigmenting preparations, e.g. preparations for bleaching the skin or skin-lightening preparations;

insect-repellents, e.g. insect-repellent oils, lotions, sprays or sticks;

deodorants, such as deodorant sprays, pump-action sprays, deodorant gels, sticks or roll-ons;

antiperspirants, e.g. antiperspirant sticks, creams or roll-ons;

preparations for cleansing and caring for blemished skin, e.g. synthetic detergents (solid or liquid), peeling or scrub preparations or peeling masks;

hair-removal preparations in chemical form (depilation), e.g. hair-removing powders, liquid hair-removing preparations, cream- or paste-form hair-removing preparations, hair-removing preparations in gel form or aerosol foams;

shaving preparations, e.g. shaving soap, foaming shaving creams, non-foaming shaving creams, foams and gels, preshave preparations for dry shaving, aftershaves or aftershave lotions;

fragrance preparations, e.g. fragrances (eau de Cologne, eau de toilette, eau de parfum, parfum de toilette, parfume), parfume oils or parfume creams;

cosmetic hair-treatment preparations, e.g. hair-washing preparations in the form of shampoos and conditioners, hair-care preparations, e.g. pre-treatment preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straight-ening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colorants, preparations containing self-oxidising dyes, or natural hair colorants, such as henna or camomile.

The final formulations listed may exist in a wide variety of presentation forms, for example:

in the form of liquid preparations as a W/O, O/W, O/W/O, W/O/W or PIT emulsion and all kinds of microemulsions, in the form of a gel, in the form of an oil, a cream, milk or lotion, in the form of a powder, a lacquer, a tablet or make-up, in the form of a stick, in the form of a spray (spray with propellant gas or pump-action spray) or an aerosol, in the form of a foam, or in the form of a paste.

Important cosmetic compositions for the skin are light-protective preparations, such as sun milks, lotions, creams, oils, sunblocks or tropicals, pretanning preparations or after-sun preparations, also skin-tanning preparations, for example self-tanning creams. Of particular interest are sun protection creams, sun protection lotions, sun protection oils, sun protection milks and sun protection preparations in the form of a spray.

Important cosmetic compositions for the hair are the above-mentioned preparations for hair treatment, especially hair-washing preparations in the form of shampoos, hair conditioners, hair-care preparations, e.g. pretreatment preparations, hair tonics, styling creams, styling gels, pomades, hair rinses, treatment packs, intensive hair treatments, hair-straightening preparations, liquid hair-setting preparations, hair foams and hairsprays. Of special interest are hair-washing preparations in the form of shampoos.

A shampoo has, for example, the following composition:
0.01 to 5% by weight of a UV absorber composition according to the invention,
12.0% by weight of sodium laureth-2-sulfate,
4.0% by weight of cocamidopropyl betaine,
3.0% by weight of sodium chloride, and
water ad 100%.

Especially the following hair-cosmetic formulations may be used:

$a_1$) spontaneously emulsifying stock formulation, consisting of the UV absorber according to the invention, PEG-6-$C_{10}$oxoalcohol and sorbitan sesquioleate, to which water and any desired quaternary ammonium compound, for example 4% minkamidopropyl-dimethyl-2-hydroxyethylammonium chloride or Quaternium 80 is added;

$a_2$) spontaneously emulsifying stock formulation consisting of the UV absorber according to the invention, tributyl citrate and PEG-20-sorbitan monooleate, to which water and any desired quaternary ammonium compound, for example 4% minkamidopropyl-dimethyl-2-hydroxyethylammonium chloride or Quaternium 80 is added;

b) Quat-doped solutions of the UV absorber according to the invention in butyltriglycol and tributyl citrate;

c) mixtures or solutions of the UV absorber according to the invention with n-alkylpyrrolidone.

Suitable cosmetically acceptable auxiliaries are also described in in Fiedler, H. P. Lexikon der Hilfsstoffe für Pharmazie, Kosmetik und angrenzende Gebiete [Lexicon of the auxiliaries for pharmacy, cosmetics and related fields], 4th edition, Aulendorf: ECV-Editio-Kantor-Verlag, 1996.

The polyvinyl alcohol used as core surrounding layer of the capsule shell according the present invention is obtainable by polymerization of vinyl acetate, optionally in the presence of comonomers, and hydrolysis of the polyvinyl acetate with elimination of the acetyl groups to form hydroxy groups. The preparation of copolymers of vinyl acetate, and the hydrolysis of these polymers for the formation of polymers comprising vinyl alcohol units are generally known.

Preferred are anionic polyvinyl alcohols. The term 'anionic polyvinyl alcohol' refers to polyvinyl alcohols which carry acid groups (according to Broenstedt definition) . Depending on the pH of the water phase the acid groups in the polymer are protonated or deprotonated. Anionic polyvinylalcohols are copolymers of vinyl alcohol/vinyl acetate and anionic comonomers (comonomers with acid groups).

The acid groups of the polyvinyl alcohol are preferably selected from the group consisting of sulfonic acid groups, phosphonic acid groups and carboxylic acids groups comprising 3 to 8 carbon atoms in a molecule, and/or the alkali metal, alkaline earth metal or ammonium salts thereof.

The anionic polyvinyl alcohol comprises, for example, from 0.1 to 30 mol %, in general from 0.5 to 20 mol %, preferably from 1 to 10 mol % of at least one of said comonomers incorporated in the form of polymerized units.

The preferred anionic polyvinyl alcohol according the present invention is obtainable by polymerization of vinyl acetate, optionally in the presence of comonomers carrying acid groups, and hydrolysis of the polyvinyl acetate with elimination of the acetyl groups to form hydroxy groups. The preparation of copolymers of vinyl acetate and the hydrolysis of these polymers to form polymers comprising vinyl alcohol units are generally known.

There are several ways to introduce the acid group. According to one preferred method the acid function is introduced by copolymerization of vinylacetate with a comonomer carrying acid groups preferably selected from monoethylenically unsaturated sulfonic acids, monoethylenically unsaturated phosphonic acids and monoethylenically unsaturated carboxylic acids having 3 to 8 carbon atoms in a molecule and/or the alkali metal, alkaline earth metal or ammonium salts thereof.

Preferred acid groups are selected from the group consisting of sulfonic acid and carboxylic acid having 3 to 8 carbon atoms in a molecule and/or the alkali metal, alkaline earth metal or ammonium salts thereof.

Examples of monomers carrying acid functions which result in the acid groups are ethylenically unsaturated $C_3$- to $C_8$-carboxylic acids, such as, for example, acrylic acid, methacrylic acid, dimethacrylic acid, ethacrylic acid, maleic acid, fumaric acid, itaconic acid, mesaconic acid, citraconic acid, methylenemalonic acid, allylacetic acid, vinylacetic acid and crotonic acid. Other suitable monomers of this group are monomers comprising sulfo groups, such as vinylsulfonic acid, acrylamido-2-methylpropanesulfonic acid and styrene sulfonic acid, and monomers comprising phosphonic groups, such as vinyl phosphonic acid. Preferred monomers are itaconic acid, maleic acid, acrylic acid and methacrylic acid. The monomers of this group can be used alone or as a mixture with one another, in partly or in completely neutralized form in the copolymerization. For example, alkali metal or alkaline earth metal bases, ammonia, are used for the neutralization. Examples of these are sodium hydroxide solution, potassium hydroxide solution, sodium carbonate, potassium carbonate, sodium bicarbonate, magnesium oxide, calcium hydroxide, calcium oxide.

Alternatively the acid groups may be introduced into a polyvinyl alcohol by a postmodification reaction.

Preference is given to polyvinyl alcohols, especially anionic polyvinyl alcohol, the viscosity of which for a 4% strength by weight aqueous solution at 20° C. in accordance with DIN 53015 has a value in the range from 1.5 to 70 mPa·s, preferably a value from 15 to 35 mPa·s.

Preference is given to polyvinyl alcohols, preferably anionic polyvinyl alcohol with a degree of hydrolysis of from 60 to 100%, preferably 79 to 95%, in particular 80 to 90% in accordance with DIN 53401.

Polyvinyl alcohols, especially anionic polyvinyl alcohol with hydrolysis degrees from 85 to 99.9, especially 85% to 95% are preferred, containing 0.1 to 30 mol % comonomers with acid functions like carboxyl- and/or sulfonic acid groups, wherein mol % is based on the polymerization mixture vinyl acetate/comonomer.

Anionic polyvinyl alcohols are sold for example as Mowiol® grades from Kuraray Specialities Europe (KSE).

Preferred are anionic polyvinyl alcohol with a hydrolysis degree of 85.0%-99.5% and a viscosity of 2 mPas-70 mPas. Examples of such type of colloids are: K-Polymer KL-318 from Kuraray (viscosity 20-30 mPas, hydrolysis 85.0-90.0%), Gohsenal T-350 from Nippon Gohsei (viscosity 27-33 mPas, hydrolysis 93.0-95.0%), Gohseran L-3266 from Nippon Gohsei (viscosity 2.3-2.7 mPas, hydrolysis 86.5-89.0%).

Particular protective colloids include polyvinyl alcohol homopolymers.

It is known that polyvinyl alcohol is produced by hydrolysis (deacetylation) of polyvinylacetate, whereby ester groups of polyvinyl acetate are hydrolyzed into hydroxyl groups, thus forming polyvinyl alcohol.

The degree of hydrolysis reflects the percentage of groups that are converted by hydrolysis. The term "polyvinyl alcohol", qualified by a degree of hydrolysis, means therefore, a vinyl polymer containing both ester and hydroxyl groups.

The degree of hydrolysis can be determined by techniques well known in the art, for example, according to DIN 53401.

Preferred are polyvinyl alcohol homopolymers with a hydrolysis degree of 85.0%-99.5% and a viscosity of 2 mPas-70 mPas. Examples of such type of colloids are Kuraray Poval such as Poval 8-88, Poval 18-88, Poval 26-88, Poval 6-98.

Polyoxazolines have been subject of considerable amount of research since the 1960s and processes for the preparation of polyoxazolines are known in the art. The polyoxazoline according to the invention is a polymer which consists of a polymerized form of oxazoline monomer (A) and optionally one or more further oxazoline monomers (B). The polyoxazolines preferably have a polydispersity $M_w/M_n$, whereas $M_w$ refers to the weight average molecular weight and $M_n$ refers to the number average molecular weight between 1 and 3. $M_n$ of such polyoxazolines is usually between 500 and 500,000, preferably 1,000 and 10,000 and more preferably 1,000 and 5,000. The polyoxazolines can be in the form of block polymers with controlled block lengths, random copolymers, graft polymers, comb polymers, star polymers, polymers with functional end-groups including, but not limited, to macromonomers and telechelic polymers etc.

Preferred are oxazoline monomers (A) corresponding to formula (I)

wherein R is selected from hydrogen and linear or branched alkyl.

The additional oxazoline monomer (B) is preferably an oxazoline monomer (B) according to formula (I), wherein R of monomer (B) is selected from hydrogen and linear or branched alkyl, but is different from R of monomer (A).

In a preferred embodiment in the above formula (I), R is selected from hydrogen and linear or branched $C_1$-$C_4$ alkyl.

In a more preferred embodiment the oxazoline monomer is selected from methyl oxazoline, ethyl oxazoline, propyl oxazoline, isopropenyl oxazoline and butyl oxazoline. In an even more preferred embodiment the oxazoline monomer is 2-ethyl-2-oxazoline. Further preferred is statistical ethylmethyl polyoxazoline, for example Poly-(ethyl-stat.methyl)-oxazoline (4:1)

Polyoxazolines are known. A process for their preparation is described in PCT/EP 2014/05925, the disclosure of which is incorporated herewith by reference. The polymerization process is considered to be a "living polymerization". In living polymerizations, the polymerization of the monomer progresses until the monomer is virtually exhausted and upon addition of further monomer or a different monomer the polymerization resumes. In living polymerization the degree of polymerization and hence the molecular weight can be controlled by the monomer and initiator concentrations.

The present invention further relates to a process for producing microcapsules comprising a capsule shell and a capsule core, comprising the process steps:

a) preparation of an oil-in-water emulsion with a disperse phase which comprises the core material and an aqueous continuous phase and an polyvinyl alcohol, preferably an anionic polyvinyl alcohol, and b) subsequent addition of one or more polyoxazoline.

The size of the droplet of the core substance obtained by distribution is related to the size of the microcapsule obtained. The size of a microcapsule is chosen according to the purpose, and the size of the droplet of an emulsion is substantially reflected as particle diameter of the microcapsule.

The microcapsules may be present in the form of an aqueous dispersion, wherein the fraction of the capsules may be from 1 to 90% by weight, but preferably from 5 to 50% by weight.

According the process of the present invention it is not necessary to add additional surface-active substances, such as polymeric protective colloids in order to obtain a stable emulsion.

Protective colloids, which may be ionic or neutral may be added if desired.

Preference is given to use organically neutral protective colloids which are preferably water-soluble polymers. Organic neutral protective colloids are, for example, cellulose derivatives such as hydroxyethylcellulose, methylhydroxyethylcellulose, methylcellulose and carboxymethylcellulose, polyvinylpyrrolidone, copolymers of vinylpyrrolidone, gelatin, gum arabic, xanthan, casein, polyethylene glycols and methylhydroxypropylcellulose.

In addition, for costabilization purposes it is possible to add surfactants, preferably nonionic surfactants. Suitable surfactants can be found in the "Handbook of Industrial Surfactants", to the contents of which reference is expressly made. The surfactants may be used in an amount of from 0.01 to 10% by weight, based on the water phase of the emulsion.

A stable emulsion of core material and polyvinyl alcohol in water is prepared with stirring. In this case, stable means that it does not result in a doubling of the average droplet size within one hour.

As a rule, the emulsion is formed at a neutral pH of the water phase, but may also be acidic or alkaline depending on the core material.

Preferably, the dispersing conditions for manufacturing the stable oil-in-water emulsion are selected in a manner known per se such that the oil droplets have the size of the desired microcapsules. Even small capsules, which size is to be below 5 μm, might be obtained by using standard stirring devices such as anchor stirrers or Intermig or propeller stirrers. It is further possible to use homogenizing or dispersing machines, in which case these units may be provided with or without a forced-flow device.

The capsule size may be controlled within certain limits via the rotational speed of the dispersing device/homogenizing device and/or with the support of the concentration of the protective colloid or via its molecular weight, i.e. via the viscosity of the aqueous continuous phase. In the context of the present invention the size of the dispersed droplets decreases, since the rotational speed increases up to a limiting rotational speed.

In this connection the dispersing devices are preferably used at the start of capsule formation. In the case of continuously operating devices with forced flow it is advantageous to send the emulsion several times through the shear field.

In order to disperse highly viscous thermally stable media the preparation of the emulsion takes place within a temperature range from 30 to 130° C., preferably 40 to 100° C.

As a rule, the coacervation is carried out at 15 to 100° C., preferably at 20 to 40° C. Depending on the preferred core material the oil-in-water emulsion is to be formed at a temperature at which the core material is liquid/oily.

As a rule the preparation of the emulsion takes place at a pH from 1 to 7, preferably 2 to 5. It is further preferred to add the one or more polyoxazolines at a pH from 1 to 7, preferably 2 to 5.

Preferably the amount of the core material is from 1 to 50% by weight, preferably 5 to 40% by weight, based on the resulting microcapsule dispersion which equals the amount of all ingredients.

In a preferred process the oil-in-water emulsion comprises 0.1 to 10% by weight, preferably 1 to 5% by weight, more preferably 2 to 5% by weight, of polyvinyl alcohol, preferably anionic polyvinyl alcohol.

It is further preferred to add 0.1 to 10% by weight, preferably 1 to 5% by weight, more preferably 2 to 5% by weight based on the oil-in-water emulsion, of a polyoxazoline.

A preferred process for producing microcapsules comprises the process steps:
a) preparation of an oil-in-water emulsion with a disperse phase which comprises the core material and an aqueous continuous phase and 0.1 to 10% by weight, based on the oil-in-water emulsion, of an anionic polyvinyl alcohol and
b) subsequent addition of 0.1 to 10% by weight, based on the oil-in-water emulsion, of one or more polyoxazoline(s).

The present invention further relates to aqueous dispersions comprising 5 to 50% by weight, based on the total weight of the dispersion, preferably from 15 to 40% by weight, of microcapsules which can be produced by the above process. A further preferred range is between 20 and 35% by weight. These aqueous dispersions are preferably obtained directly from the process described above.

The microcapsule dispersions which are obtained by the process according to the present invention may be used in a large number of different applications, depending on the type of core material.

For example the microcapsules may be used for the finishing of all kind of nonwovens like wipes (for example wet wipes or dry wipes for cosmetic or cleaning purposes), but also for finishing papers (including wallpapers, toilet paper or papers for books and newsletters), for finishing diapers or sanitary napkins and similar hygienic products or textiles, e.g. in order to finish the papers or textiles with a dye or an insecticide.

Another use pertains to the finishing of diapers or sanitary napkins and similar hygienic products.

EXAMPLES

The particle size of the microcapsule dispersion is determined using a Malvern Particle Sizer model 3600E or a Malvern Mastersizer 2000 in accordance with a standard measuring method which is documented in the literature. The D[v, 0.1] value means that 10% of the particles have a particle size (in accordance with the volume average) up to this value. Accordingly, D[v, 0.5] means that 50% of the particles and D[v, 0.9] means that 90% of the particles have a particle size (according to the volume average) less than/equal to this value. The span value arises from the quotient from the difference D[v, 0.9]–D[v, 0.1] and D[v, 0.5]. The D[4.3] value is the weight-average.

Measurement of the Solid Content

The fraction of nonvolatile components (solid content) of the resulting dispersion is measured with a Ohaus Halogen Moisture Analyzer. The instrument operates on the thermogravimetric principle: the sample is heated to weight constant (drying temperature: 140° C.).

Leakage Evaluation

For the leakage evaluation a known amount of capsule dispersion is stored for 3 days in 5 weight % sodium dodecyl sulfate solution (SDS) at 50° C. temperature. After this time the slurry is extracted 3 times with cyclohexane. Next, the solvent is evaporated and the residue is gravimetrically analyzed.

Capsules Dispersion Stability Shelf-Life Evaluation

The capsule dispersion is stored at room temperature (20° C.) for 3 month in the graduated measuring glass. After this time the separation of dispersion is quantitatively measured.

Viscosity

Viscosity values of PVAs are the values of a 4 weight % aqueous solution determined at 20° C. by Brookfield viscometer.

Encapsulation of Perfume Oils

Example 1

A premix (I) containing 12.5 g of itaconic acid-modified anionic PVA (Mowiol® KL-318, Kuraray with hydrolysis degree 85%-90% and visc. 20.0-30.0 mPas) and 274.2 g of water is prepared. Next it is poured into 150 g of Citronellyl isobutyrate and emulsified with the help of a Mig stirrer at room temperature for 30 minutes at a speed of 800 rpm. Premix (II) containing 19.2 g of (Poly-(ethyl-stat.-methyl)-oxazoline (4:1)) and 17.8 g of water is prepared. Premix (II) is next added to the emulsion of premix (I) and Citronellyl isobutyrate over the course of 5 minutes. The reaction mixture is then stirred at room temperature for 30 minutes resulting in the desired microcapsule dispersion with a fraction of nonvolatile components of 37.9% and a particle size distribution according to the following values: d 50=7 μm and d 90=9 μm.

Example 2

A premix (I) is prepared from 12.5 g of itaconic acid-modified anionic PVA (Mowiol® KL-318, Kuraray with hydrolysis degree 85%-90% and visc. 20.0-30.0 mPas) and 274.2 g of water. Next it is poured into 150 g of Ethyl laurate and emulsified with the support of a Mig stirrer at room temperature for 30 minutes at a speed of 700 rpm. Premix (II) is prepared from 19.2 g of (Poly-(ethyl-stat.-methyl)-oxazolin(4:1)) and 17.8 g of water. Next it is added to the formed emulsion of premix (I) and Ethyl laurate over the course of 5 minutes. The reaction mixture is then stirred at room temperature for 30 minutes resulting in the desired microcapsule dispersion with a fraction of nonvolatile components of 38.1% and a particle size distribution according to the following values: d 50=9 μm and d 90=15 μm.

Example 3

150 g of DL-Menthol is pre-heated to 40° C. A premix (I) is prepared from 12.5 g of itaconic acid-modified anionic PVA (Mowiol® KL-318, Kuraray with hydrolysis degree 85%-90% and visc. 20.0-30.0 mPas) and 274.2 g of water. The premix (I) is heated to 40° C. and is next poured into 150 g of DL-Menthol and emulsified with help of a Mig stirrer for 50 minutes at 40° C. at a speed of 800 rpm. Premix (II) is prepared from 19.2 g of polymethyloxazoline (3.8 kg/mol) and 17.8 g of water. Next it is added to the formed emulsion of premix (I) and DL-Menthol over the course of 5 minutes. The reaction mixture is then stirred at 40° C. for 30 minutes resulting in the desired microcapsule dispersion with a fraction of nonvolatile components of 38.5% and a particle size distribution according to the following values: d 50=4 μm and d 90=9 μm.

Encapsulation of UV Filters

Example 4

A premix (I) is prepared from 12.5 g of itaconic acid-modified anionic PVA (Mowiol® KL-318, Kuraray with hydrolysis degree 85%-90% and visc. 20.0-30.0 mPas) and 274.2 g of water. Premix (II) is prepared from 58 g of Hexyl 2-[4-(diethylamino)-2-hydroxybenzoyl]benzoate (Uvinul A Plus, BASF) and 92 g of Phenoxyethylester (Tegosoft XC, Evonik). Premix (III) is prepared with 9.6 g of poly(ethyl-methyloxazoline) (Poly(ethyl-stat.-methyl)-oxazolin(4:1)), 4.2 kg/mol) and 17.8 g of water. Premix (II) is poured into Premix (I) and emulsified with help of a Mig stirrer for 30 minutes at room temperature at a speed of 800 rpm. Premix (III) is then added to the formed emulsion of premixes (I) and (II) over the course of 5 minutes. The reaction mixture is then stirred at room temperature for 30 minutes resulting in the desired microcapsule dispersion with a fraction of nonvolatile components of 36.9% and a particle size distribution according to the following values: d 50=5 μm and d 90=8 μm.

Example 5

A premix (I) is prepared from 12.5 g of itaconic acid-modified anionic PVA (Mowiol® KL-318, Kuraray with hydrolysis degree 85%-90% and visc. 20.0-30.0 mPas) and 274.2 g of water. Premix (II) is prepared from 65 g of Hexyl 2-[4-(diethylamino)-2-hydroxybenzoyl]benzoate (Uvinul A Plus, BASF) and 85 g of 2-Ethylhexylbenzoate (Finsolv EB, Innospec). Premix (III) is prepared with 19.2 g of poly (ethyl-methyloxazoline) (Poly-(ethyl-stat.-methyl)-oxazolin (4:1), 4.2 kg/mol)) and 17.8 g of water. Premix (II) is poured into Premix (1) and emulsified with help of a Mig stirrer for 30 minutes at room temperature at a speed of 800 rpm. Premix (III) is then added to the formed emulsion of premixes (I) and (II) over the course of 5 minutes. The reaction mixture is then stirred at room temperature for 10 minutes resulting in the desired microcapsule dispersion with a fraction of nonvolatile components of 37.4% and a particle size distribution according to the following values: d 50=9 μm and d 90=17 μm.

Example 6

A premix (I) is prepared from 12.5 g of itaconic acid-modified anionic PVA (Mowiol® KL-318, Kuraray with hydrolysis degree 85%-90% and visc. 20.0-30.0 mPas) and 202.89 g of water. Premix (II) is prepared from 65 g of Hexyl 2-[4-(diethylamino)-2-hydroxybenzoyl]benzoate (Uvinul A Plus, BASF) and 85 g of 2-Ethylhexylbenzoate (Finsolv EB, Innospec). Premix (III) is prepared with 38.4 g of poly (ethyl-methyloxazoline) (Poly-(ethyl-stat.-methyl)-oxazolin (4:1)), 4.2 kg/mol) and 71.31 g of water. Premix (II) is poured into Premix (I) and emulsified with help of a Mig stirrer for 30 minutes at room temperature at a speed of 850 rpm. Premix (III) is then added to the formed emulsion of premixes (I) and (II) over the course of 5 minutes. The reaction mixture is then stirred for 10 minutes at room temperature resulting in the desired microcapsule dispersion with a fraction of nonvolatile components of 42.31% and a particle size distribution according to the following values: d 50=8 μm and d 90=13 μm.

Example 7

A premix (I) is prepared from 12.5 g of itaconic acid-modified anionic PVA (Mowiol® KL-318, Kuraray with hydrolysis degree 85%-90% and visc. 20.0-30.0 mPas) and 202.89 g of water. Premix (II) is prepared from 24 g of 2,2'-[6-(4-methoxyphenyl)-1,3,5-triazine-2,4-diyl] bis{5-[(2-ethylhexyl)oxy]phenol} (Tinosorb S, BASF) and 126 g of 2-Ethylhexylbenzoate (Finsolv EB, Innospec). Premix (III) is prepared with 9.6 g of poly(ethyl-methyloxazoline) (Poly-(ethyl-stat.-methyl)-oxazolin(4:1), 4.2 kg/mol)) and 17.8 g of water. Premix (II) is poured into Premix (I) and emulsified with help of a Mig stirrer at room temperature for 30 minutes at a speed of 800 rpm. Premix (III) is then added to the formed emulsion of premixes (I) and (II) over the course of 5 minutes. The reaction mixture is then stirred at room temperature for 10 minutes resulting in the desired microcapsule dispersion with a fraction of nonvolatile components of 43.2% and a particle size distribution according to the following values: d 50=10 μm and d 90=17 μm.

Example 8

A premix (I) is prepared from 14.1 g of polyvinyl alcohol PVA (Mowiol® 18-88, Kuraray with hydrolysis degree 86.7%-88.7% and visc. 16-20 mPas) and 193.4 g of water. Premix (II) is prepared from 42.6 g of 2,2'-[6-(4-methoxyphenyl)-1,3,5-triazine-2,4-diyl]bis{5-[(2-ethylhexyl)oxy]phenol} (Tinosorb S, BASF) and 170.4 g of 2-Ethylhexyl salicylate. Premix (III) is prepared from 14.6 g of poly(2-ethyl-2-oxazoline) (Mw=50 kDa) and 38 g of water. Premix (II) is poured into Premix (I) and emulsified with help of a Mig stirrer for 30 minutes at room temperature at a speed of 800 rpm. Premix (III) is then added to the formed emulsion of premixes (I) and (II) over the course of 5 minutes. The reaction mixture is then stirred at room temperature for 10 minutes resulting in the desired microcapsule dispersion with a fraction of nonvolatile components of 49.26% and a particle size distribution according to the following values: d 50=13 μm and d 90=21 μm.

Example 9

A premix (I) is prepared from 19.5 g of polyvinyl alcohol PVA (Mowiol® 18-88, Kuraray with hydrolysis degree 86.7%-88.7% and visc. 16-20 mPas) and 267.3 g of water. Premix (II) is prepared from 35.6 g of 4-[[4,6-bis[[4-(2-ethylhexoxy-oxomethyl)phenyl]amino]-1,3,5-triazin-2-yl]amino]benzoic acid 2-ethylhexyl ester (Uvinul T150, BASF) and 114.4 g of lauryl lactate (Exceparl LM-LC, Kao Corporation S.A.). Premix (III) is prepared from 10.3 g of poly(2-ethyl-2-oxazoline) (Mw=50 kDa) and 26.8 g of water. Premix (II) is poured into Premix (I) and emulsified with help of a Ultra Turrax high shear disperser for 5 minutes at room temperature at a speed of 20000 rpm. Premix (III) is then added to the formed emulsion of premixes (I) and (II) over the course of 5 minutes. The reaction mixture is then stirred at room temperature for 10 minutes with help of a Mig stirrer at a speed of 800 rpm resulting in the desired microcapsule dispersion with a fraction of nonvolatile components of 34.16% and a particle size distribution according to the following values: d 50=1.0 μm and d 90=1.8 μm.

Example 10

A premix (I) is prepared from 12.5 g of polyvinyl alcohol PVA (Mowiol® 18-88, Kuraray with hydrolysis degree 86.7%-88.7% and visc. 16-20 mPas) and 274.2 g of water. Premix (II) is prepared from 59 g Hexyl 2-[4-(diethylamino)-2-hydroxybenzoyl]benzoate (Uvinul A Plus, BASF) and 92 g of Phenoxyethylester (Tegosoft XC, Evonik). Premix (III) is prepared from 38.4 g of poly(2-ethyl-2-oxazoline) (Mw=50 kDa) and 36 g of water. Premix (II) is poured into Premix (I) and emulsified with help of a Mig stirrer for 30 minutes at room temperature at a speed of 800 rpm. Premix (III) is then added to the formed emulsion of premixes (I) and (II) over the course of 5 minutes. The reaction mixture is then stirred at room temperature for 10 minutes resulting in the desired microcapsule dispersion with a fraction of nonvolatile components of 37.6% and a particle size distribution according to the following values: d 50=13 μm and d 90=22 μm.

Encapsulation of Cosmetic Oils

Example 11

A premix (I) is prepared from 12.5 g of itaconic acid-modified anionic PVA (Mowiol® KL-318, Kuraray with hydrolysis degree 85%-90% and visc. 20.0-30.0 mPas) and 274.2 g of water. Next it is poured into 150 g of caprylic/capric triglyceride cosmetic oil (Myritol 318, BASF) and emulsified with help of a Mig stirrer at room temperature for 30 minutes at a speed of 700 rpm. Premix (II) is prepared from 9.6 g of polyethyl-methyloxazoline (Poly-(ethyl-stat.-methyl)-oxazolin(2:3), 4.4 kg/mol)) and 17.8 g of water. It is next added to the formed emulsion of premix (I) and caprylic/capric triglyceride cosmetic oil over the course of 1 minute. The reaction mixture is then stirred at room temperature for 30 minutes resulting in the desired microcapsule dispersion with a fraction of nonvolatile components of 37.1% and a particle size distribution according to the following values: d 50=7 μm and d 90=15 μm.

Example 12

A premix (I) is prepared from 12.5 g of itaconic acid-modified anionic PVA (Mowiol® KL-318, Kuraray with hydrolysis degree 85%-90% and visc. 20.0-30.0 mPas) and 274.2 g of water. Next it is poured into 150 g of caprylic/capric triglyceride cosmetic oil (Myritol 318, BASF) and emulsified with help of a Mig stirrer for 45 minutes at room temperature at a speed of 900 rpm. Premix (II) is prepared from 9.6 g of polymethyloxazoline (3.8 kg/mol) and 17.8 g of water. Next it is added to the formed emulsion of premix (I) and caprylic/capric triglyceride cosmetic oil over the course of 5 minutes. The reaction mixture is then stirred for 30 minutes at room temperature resulting in the desired microcapsule dispersion with a fraction of nonvolatile components of 36.9% and a particle size distribution according to the following values: d 50=3 μm and d 90=6 μm.

Example 13

A premix (I) is prepared from 12.5 g of itaconic acid-modified anionic PVA (Mowiol® KL-318, Kuraray with hydrolysis degree 85%-90% and visc. 20.0-30.0 mPas) and 274.2 g of water. Next it is poured into 150 g of modified coconut oil (Myritol 331, BASF), and emulsified with help of a Mig stirrer at room temperature for 30 minutes at a speed of 700 rpm. Premix (II) is prepared from 9.6 g of (Poly-(ethyl-stat.-methyl)-oxazolin(4:1)) and 17.8 g of water. Next it is added to the formed emulsion of premix (I) and modified coconut cosmetic oil over the course of 5 minutes. The reaction mixture is then stirred for 10 minutes at room temperature resulting in the desired microcapsule dispersion with a fraction of nonvolatile components of 36.9% and a particle size distri-distribution according to the following values: d 50=8 μm and d 90=16 μm.

Formulation Examples

Cosmetic sunscreen formulations are prepared with capsule dispersions as prepared in examples 4-10.

Formulations 1, 2 and 3 comprising a capsule dispersion containing UV-filter Uvinul A Plus:

|  | Tradename | INCI-Name | amount % w/w (as supplied) | | |
|---|---|---|---|---|---|
|  |  |  | F1 | F2 | F3 |
| Part A | Uvinul ® MC 80 | Ethylhexyl Methoxy-cinnamate | 8.00 | 8.00 | 8.00 |
|  | Cetiol ® C5 | Coco-Caprylate | 4.00 | 4.00 | 4.00 |
|  | Eumulgin Prisma | Disodium Cetearyl Sulfosuccinate | 0.30 | 0.30 | 0.30 |
| Part B |  | Water | 52.3 | 52.3 | 52.3 |
| Part C | Luvigel ® EM | Caprylic/Capric Triglyceride (and) Sodium Acrylates Copolymer | 4.00 | 4.00 | 4.00 |
| Part D |  | microcapsule dispersion according to Example 4 | 30.4 |  |  |
|  |  | microcapsule dispersion according to Example 5 |  | 30.4 |  |
|  |  | microcapsule dispersion according to Example 6 |  |  | 30.4 |
|  | Protectol PE | Phenoxyethanol Specification | 1.00 | 1.00 | 1.00 |
|  | pH start |  | 5.89 | 5.82 | 5.86 |
|  | In vitro SPF Start |  | 12 | 11 | 10 |
|  | In vitro UVA-PF Start |  | 8.4 | 8.5 | 8.3 |
|  | UVA-PF/SPF |  | >1/3 | >1/3 | >1/3 |
|  | Viskosity RVT, 10 rpm, Sp 6 |  | 76720 mPa s | 32680 mPa s | 32980 mPa s |

General Procedure:

Part A: Heat up Uvinul MC 80 to 75° C.-80° C., add Cetiol C5 and Eumulgin Prisma under stirring.

Add Part B under stirring at 75° C.

Add Part C and homogenize using Turrax.

Finally add Part D under stirring.

|  | Tradename | INCI-Name | amount % w/w (as supplied) | | |
|---|---|---|---|---|---|
|  |  |  | F4 | F5 | F6 |
| Part A | Cetiol ® CC | Dicaprylyl Carbonate | 5.00 | 5.00 | 5.00 |
|  | Cetiol B | Dibutyl Adipate | 4.00 | 4.00 | 4.00 |
|  | Cetiol C5 | Coco-Caprylate | 3.00 | 3.00 | 3.00 |
|  | Sensiva SC50 | Ethylhexylglycerin | 0.50 | 0.50 | 0.50 |
|  | Uvinul ® MC 80 | Ethylhexyl Methoxycinnamate | 10.00 | 10.00 | 10.00 |
|  | Tinosorb ® S | Bis-Ethylhexyloxyphenol Methoxyphenyl Triazine | 1.80 | 1.80 | 1.80 |
| Part B |  | Water | 36.49 | 36.49 | 36.49 |
|  |  | Glycerin | 3.00 | 3.00 | 3.00 |
|  | Eumulgin SG | Sodium Stearoyl Glutamate | 0.80 | 0.80 | 0.80 |
|  | Edeta ® BD | Disodium EDTA | 0.20 | 0.20 | 0.20 |
|  | Keltrol CG-RD | Xantham Gum | 0.20 | 0.20 | 0.20 |
| Part C |  | microcapsule dispersion according to Example 4 | 34.01 |  |  |
|  |  | microcapsule dispersion according to Example 5 |  | 34.01 |  |
|  |  | microcapsule dispersion according to Example 6 |  |  | 34.01 |
|  | Protectol PE | Phenoxyethanol Specification | 1.00 | 1.00 | 1.00 |
|  | pH start |  | 7.27 | 7.26 | 6.74 |
|  | In vitro SPF Start |  | 26.4 | 21.3 | 23.6 |
|  | Viskosity RVT, 10 rpm, Sp 6 |  | 810 mPa s | 1050 mPa s | 8000 mPa s |

General Procedure:

Heat Part A to 80° C. under stirring until everything is dissolved, cool down to room temperature. Mix Part B separately under stirring. Add cooled Part A to Part B under stirring, homogenize using Turrax. Finally add Part C under stirring.

Formulation 7 comprising a capsule dispersion containing UV-filter Tinosorb S:

|  | Tradename | INCI-Name | amount % w/w (as supplied) |
|---|---|---|---|
| Part A | Uvinul MC 80 | Etlylhexyl Methoxycinnamate | 8.00 |
|  | Uvinul A Plus | Diethylamino Hydroxybenzoyl Hexyl Benzoate | 4.00 |
|  | Cetiol C5 | Coco-Caprylate | 4.00 |
|  | Eumulgin Prisma | Disodium Cetearyl Sulfosuccinate | 0.30 |
| Part B |  | Water | 69.7 |
| Part C | Luvigel EM | Caprylic/Capric Triglyceride (and) Sodium Acrylates Copolymer | 3.00 |
| Part D |  | Microcapsule dispersion according to Example 7 | 10.00 |
|  | Protectol PE | Phenoxyethanol Specification | 1.00 |
|  | pH start |  | 6.01 |
|  | In vitro SPF Start |  | 9 |
|  | In vitro UVA-PF Start |  | 9.1 |
|  | UVA-PF/SPF |  | >1/3 |
|  | Viskosity RVT, 10 rpm, Sp 6 |  | 24820 mPa s |

Manufacturing Instruction:

Part A: Heat up Uvinul MC 80 and Uvinul A Plus under stirring to 75° C.-80° C. until dissolved, add Cetiol C5 and Eumulgin Prisma under stirring. Add Part B under stirring at 75° C. Add Part C and homogenize using Turrax. Finally add Part D under stirring.

Formulation 8 comprising a capsule dispersion containing cosmetic oil Myritol 318:

|  | Trade name | INCI-Name | amount % w/w (as supplied) |
|---|---|---|---|
| Part A | Cetiol CC | Dicaprylyl Carbonate | 5.00 |
|  | Cetiol B | Dibutyl Adipate | 4.00 |
|  | Cetiol C5 | Coco-Caprylate | 3.00 |
|  | Sensiva SC50 | Ethylhexylglycerin | 0.50 |

-continued

| | Trade name | INCI-Name | amount % w/w (as supplied) |
|---|---|---|---|
| | Uvinul MC 80 | Ethylhexyl Methoxycinnamate | 10.00 |
| | Uvinul A Plus | Diethylamino Hydroxybenzoyl Hexyl Benzoate | 4.00 |
| | Tinosorb S | Bis-Ethylhexyloxyphenol Methoxyphenyl Triazine | 1.80 |
| Part B | | Water | 31.49 |
| | | Glycerin | 3.00 |
| | Eumulgin SG | Sodium Stearoyl Glutamate | 0.80 |
| | Edeta BD | Disodium EDTA | 0.20 |
| | Keltrol CG-RD | Xantham Gum | 0.20 |
| Part C | Tinovis ADE | Sodium Acrylates Copolymer (and) Hydrogenated Polydecene (and) PPG-1 Trideceth-6 | 1.00 |
| Part D | | Capsule dispersion according to Example 11 | 34.01 |
| | Protectol PE | Phenoxyethanol | 1.00 |
| | | NaOH 30% Specification | 0.38 |

| pH start | 7.04 |
|---|---|
| In vitro SPF Start | 32.2 |
| Viskosität RVT, 10 rpm, Sp 6 | 9880 mPa s |

Manufacturing Instruction:

Heat Part A to 80° C. under stirring until everything is dissolved, cool down to room temperature. Mix Part B separately under stirring. Add cooled Part A to Part B under stirring, homogenize using Turrax. Add Part C using Turrax. Finally add Part D under stirring.

Formulation 9 comprising a capsule dispersion containing UV-filter Uvinul A Plus (prepared according to example 10):

| | Tradename | INCI-Name | Amount % w/w (as supplied) |
|---|---|---|---|
| | Cetiol C5 | Coco-Caprylate | 4.00 |
| | Eumulgin Prisma | Disodium Cetearyl Sulfosuccinate | 0.30 |
| B | | Water | 58.47 |
| C | Luvigel EM | Caprylic/Capric Triglyceride (and) Sodium Acrylates Copolymer | 4.00 |
| | | microcapsule dispersion according to Example 10 | 32.23 |
| | Protectol PE | Phenoxyethanol Specification | 1.00 |

| pH start | 5.90 |
|---|---|
| UVA-PF (ISO 24442) | 8.3 |
| UVA-PF/SPF | 2.52 (passed) |
| Viskosität RVT, 10 rpm, Sp 6 | 18400 mPa s |

Manufacturing Instruction:

Part A: Heat up Cetiol C5 to 75° C.-80° C. and add Eumulgin Prisma under stirring.

Add Part B under stirring at 75° C.

Add Part C and homogenize using Turrax.

Finally add Part D under stirring.

Formulation 10 comprising a capsule dispersion containing UV-filter Uvinul A Plus (prepared according to example 10):

| | Tradename | INCI-Name | Amount % w/w (as supplied) |
|---|---|---|---|
| Part A | | Water | 64.16 |
| | Tinovis GTC | Acrylates/Beheneth-25 Methacrylate Copolymer | 2.00 |
| | | NaOH 30% ig | 0.30 |
| Part B | Tinosorb M | Methylene Bis-Benzotriazolyl Tetramethylbutylphenol (nano) | 2.00 |
| | Tinosorb A2B | Tris-Biphenyl Triazine | 2.00 |
| Part C | | microcapsule dispersion according to Example 10 | 28.84 |
| | Protectol PE | Phenoxyethanol Specification | 1.00 |

| pH start | 7.10 |
|---|---|
| In silico SPF | 9.8 |
| In vitro SPF | 6 |
| In vitro UVAPF (after irridiation) | 20.8 |
| Colipa ratio SPF/UVAPF ≤3 | passed |
| Viskosität RVT, 10 rpm, Sp 6 | 14460 mPa s |

Manufacturing Instruction:

Part A: Mix water with Tinovis GTC at room temperature, set pH to 7 with NaOH (10-30% ig).

Add Part B under stirring at RT, use Turrax if necessary. Control pH.

Add Part C under stirring.

Formulation 11 comprising a capsule dispersion containing UV-filter Uvinul A Plus (prepared according to Example 10):

| | Tradename | INCI-Name | Amount % w/w (as supplied) |
|---|---|---|---|
| Part A | Dehymuls LE | PEG-30 Dipolyhdroxystearate | 3.00 |
| | Cetiol CC | Dicaprylyl Carbonate | 5.00 |
| | Uvinul MC 80 | Ethylhexyl Methoxycinnamate | 10.00 |
| | Uvinul A Plus | Diethylamino Hydroxybenzoyl Hexyl benzoate | 2.0 |
| | Neo Heliopan OS | Ethylhexyl Salicylate | 5.00 |
| Part B | | Water | 8.30 |
| | | Glycerin | 2.00 |
| | Sodium Chloride | | 1.00 |
| | Edeta BD | Disodium EDTA | 0.20 |
| Part C | Tinosorb S Aqua | Aqua, Bis-Ethylhexyloxyphenol Methoxyphenyl Triazine, Polymethyl Methacrylate, Sodium Laureth Sulfate, Aminomethyl Propanol | 5.00 |
| Part D | | microcapsule dispersion according to Example 10 | 34.00 |
| | Xiameter PMX-0245 Cyclopentasiloxane | Cyclopentasiloxane Specification | 10.00 |

| pH start | 7.06 |
|---|---|
| SPF (ISO 24444): | 43.7 |
| UVA-PF/SPF: | 0.36 (passed) |

Manufacturing Instruction:

Heat phase A and B to 80° C. under stirring. Without Cosmedia Gel CC.

Add Cosmedia Gel CC in phase A under turrax. Then add phase B into A under stirring, homogenize.

Add phase C under stirring.

Cool down to room temperature under stirring.

Add ingredients of phase D under stirring.

Continue stirring for a while.

Formulation 12 comprising a capsule dispersion containing UV-filter Tinosorb S (prepared according to example 8):

|   | Tradename | INCI-Name | Amount % w/w (as supplied) |
|---|---|---|---|
| Part A | Cetiol CC | Dicaprylyl Carbonate | 5.00 |
|   | Cetitol B | Dibutyl Adipate | 4.00 |
|   | Cetiol C5 | Coco-Caprylate | 3.00 |
|   | Sensiva SC50 | Ethylhexylglycerin | 0.50 |
|   | Uvinul MC 80 | Ethylhexyl Methoxycinnamate | 10.00 |
|   | Uvinul A Plus | Diethylamino Hydroxybenzoyl Hexyl benzoate | 4.00 |
|   | Tinosorb S | Bis-Ethylhexyloxyphenol Methoxyphenyl Triazine | 0.8 |
| Part B |   | Water | 32.99 |
|   |   | Glycerin | 3.00 |
|   | Eumulgin SG | Sodium Stearoyl Glutamate | 0.80 |
|   | Edeta BD | Disodium EDTA | 0.20 |
|   | Keltrol CG-RD | Xantan Gum | 0.20 |
| Part C | Tinovis ADE | Sodium Acrylates Copolymer (and) hydrogenated Polydecane (and) PPG-1 Trideceth-6 | 0.5 |
| Part D |   | microcapsule dispersion according to Example 8 | 34.01 |
|   | Protectol PE | Phenoxyethanol | 1.00 |
|   |   | NaOH 30% | 0.15 |

Specification

| pH start | 7.06 |
|---|---|
| SPF (ISO 24444): | 25.7 |
| UVA-PF/SPF: | 0.46 (passed) |
| Viskosität RVT, 10 rpm, Sp 6 | 4500 mPa s |

Manufacturing Instruction:

Heat Part A to 80° C. under stirring until everything is dissolved, cool down to room temperature.

Mix Part B separately under stirring.

Add cooled Part A to Part B under stirring, homogenize using Turrax.

Add Part C using Turrax.

Finally add Part D under stirring.

Formulations 13 comprising a capsule dispersion containing UV-filter Tinosorb S (prepared according to example 8):

|   | Tradename | INCI-Name | Amount % w/w (as supplied) |
|---|---|---|---|
| Part A | Eumulgin SG | Sodium Stearoyl Glutamate | 2.00 |
|   | Cetiol AB | C12-15 Alkyl Benzoate | 5.00 |
|   | Cetiol B | Dibutyl Adipate | 5.00 |
|   | Uvinul N 539T | Octocrylene | 10.00 |
|   | Neoheliopan OS | Ethylhexyl Salicylate | 5.00 |
|   | Parsol 1789 | Butyl Methoxydibenzoylmethane | 5.00 |
|   | Uvinul A Plus | Diethylamino Hydroxybenzoyl Hexyl benzoate | 4.90 |
|   | Thinosorb S | Bis-Ethylhexyloxyphenol Methoxyphenyl Triazine | 3.00 |
|   |   | Preservative | qs |
| Part B |   | Water | 28.80 |
|   | Rheocare TTA | Acrylates Copolymer | 0.50 |
|   | Edeta BD | Disodium EDTA | 0.20 |
|   | Pemulen TR-2 Polymeric Emulsifier | Acrylates/C10-30 Alkyl Acrylate Crosspolymer | 0.10 |
| Part C |   | Water Aqua | 5.00 |
|   | Eusolex 232 | Phenylbenzimidazole Sulfonic Acid | 1.50 |
|   | Tris Amino Ultra PC | Trometamine | qs |

|   | Tradename | INCI-Name | Amount % w/w (as supplied) |
|---|---|---|---|
| D |   | microcapsule dispersion according to Example 8 | 20.00 |
|   | Cetiol Ultimate | Undecane, Tridecane | 4.00 |

Specification

| pH start | 7.0-7.4 |
|---|---|
| SPF (ISO 24444): | 57.3 |
| UVA-PF/SPF: | 0.77 (passed) |
| Viskosität RVT, 10 rpm, Sp 6 | 280 mPas |

Manufacturing Instruction:

Heat phase A and B to 80° C. under stirring. Add phase A into B under stirring, homogenize. Add phase C previously mixed under homogenizer. Cool down to room temperature under stirring. Then add part D and continue stirring for a while.

Specifications:

Formulations 14 comprising a capsule dispersion containing UV-filter Uvinul T 150 (example 9):

|   | Tradename | INCI-Name | Amount % w/w (as supplied) |
|---|---|---|---|
| Part A | Lanette O | Cetyl Stearyl Alcohol | 1 |
|   | Eumulgin SG | Sodium Stearoyl Glutamate | 2 |
|   | Cetiol B | Dibutyl Adipate | 2 |
|   | Uvinul MC80 | Ethylhexyl Methoxycinnamate |   |
|   | Uvinul A Plus | Diethylamino Hydroxybenzoyl Hexyl benzoate | 7 |
| Part B |   | Water, demin. | 35.8 |
|   |   | Glycerin | 3 |
|   | Edeta BD | Disodium EDTA | 0.2 |
| Part C | Tinovis ADE | Sodium Acrylates Copolymer (and) hydrogenated Polydecane (and) PPG-1 Trideceth-6 | 2 |
| Part D |   | microcapsule dispersion (example 9) | 40.00 |
|   | Protectol PE | Phenoxyethanol | 1 |
|   |   | NaOH 30% ig | 1.50 |

Specification

|   | Formulation 14 |
|---|---|
| pH start | 6.78 |
| In vitro SPF | 26.5 |
| Viskosität RVT, 10 rpm, Sp 6 | 18600 mPa s |

Manufacturing Instruction:

Warm up Part A and Part B separately to 80° C. until dissolution. Add Part A under stirring to Part B. Add Part C using Turray. Add Part D under stirring. Set pH to appr. 6.5.

The invention claimed is:

1. A microcapsule comprising a capsule core comprising a core material and a capsule shell wherein the capsule shell consists of a core surrounding layer consisting of a polyvinyl alcohol and an adjacent layer consisting of a polyoxazoline;
wherein the core material is one or more oil soluble UV filters (o) selected from the group consisting of
($o_1$) p-amino benzoic acid derivatives,
($o_2$) salicyl acid derivatives,
($o_3$) benzophenone derivatives,
($o_4$) dibenzoylmethane derivatives,
($o_5$) diphenylacrylates,
($o_6$) 3-imidazol-4-yl-acryl acid and their esters;
($o_7$) benzofurane derivatives;
($o_8$) polymeric UV filters;
($o_9$) cinnamic acid derivatives;

($o_{10}$) camphor derivatives;
($o_{11}$) hydroxyphenyl triazine derivates;
($o_{12}$) benzotriazole derivatives;
($o_{13}$) trianilino-s-triazine derivatives;
($o_{14}$) menthyl o-aminobenzoates;
($o_{15}$) homosalates;
($o_{16}$) benzylidene malonates;
($o_{17}$) merocyaninederivatives;
($o_{18}$) phenylene bis diphenyl triazines;
($o_{19}$) imidazoline derivatives; and
($o_{20}$) diaryl butadiene derivatives.

2. The microcapsule according to claim 1 wherein the capsule core comprises more than 95% by weight of the core material.

3. The microcapsule according to claim 1 wherein the capsule core is liquid at room temperature.

4. The microcapsule according to claim 1 wherein the average particle size of the capsule is from 0.5 to 80 µm.

5. The microcapsule according to claim 1 wherein the weight ratio of capsule core to capsule shell is in the range from 50:50 to 95:5.

6. The microcapsule according claim 1 wherein the polyvinyl alcohol is an anionic polyvinyl alcohol.

7. The microcapsule according to claim 1, wherein the one or more oil soluble UV filters (o) are selected from the group consisting of
($o_{SOL-1}$) Benzophenone-3 (BP3);
($o_{SOL-2}$) Benzophenone-4 (BP4);
($o_{SOL-3}$) 3-Benzydilene Camphor (3BC);
($o_{SOL-4}$) Bis-Ethylhexyloxyphenol Methoxyphenyl Triazine (BEMT);
($o_{SOL-5}$) Butyl Methoxydibenzoylmethane (BMBM);
($o_{SOL-6}$) Diethylhexyl Butamido Triazone (DBT);
($o_{SOL-7}$) Drometrizole Trisiloxane (DTS);
($o_{SOL-8}$) Ethylhexyl Triazone (EHT);
($o_{SOL-9}$) Ethylhexyl Methoxycinnamate;
($o_{SOL-10}$) Benzylidene malonate (BM);
($o_{SOL-11}$) Diethylamino Hydroxy Benzoyl Hexyl Benzoate (DHHB);
($o_{SOL-12}$) Octocrylene;
($o_{SOL-13}$) Polysilicon-15;
($o_{SOL-14}$) Homosalate; and
($o_{SOL-15}$) Ethylhexyl salicylate.

8. The microcapsule according to claim 1, wherein the one or more oil soluble UV filters (o) are selected from the group consisting of
($o_{9a}$) Ethylhexyl Methoxycinnamate,
($o_{11a}$) Bis-Ethylhexyloxyphenol Methoxyphenyl Triazine,
($o_{13a}$) Ethylhexyl Triazone and
($o_{3a}$) Diethylamino Hydroxy Benzoyl Hexyl Benzoate.

9. The microcapsule according to claim 1, wherein the polyvinyl alcohol is an anionic polyvinyl alcohol which acid groups are selected from the group consisting of sulfonic acid groups, phosphonic acid groups and carboxylic acids groups having 3 to 8 carbon atoms in a molecule, and/or the alkali metal, alkaline earth metal or ammonium salts thereof.

10. The microcapsule according to claim 1, wherein the polyvinyl alcohol is an anionic polyvinyl alcohol with a degree of hydrolysis of from 60 to 100%.

11. The microcapsule according to claim 1, wherein the polyoxazoline consists of a polymerized form of oxazoline monomer (A) according to formula (I)

(I)

wherein R is selected from the group consisting of hydrogen, linear or branched alkyl and optionally one or more further oxazoline monomer (B) of formula (I), wherein the R of monomer (B) is selected from the group consisting of hydrogen, linear or branched alkyl but is different from the R of monomer (A).

12. An aqueous dispersion comprising 5 to 50% by weight, based on the total weight of the dispersion, of microcapsules according to claim 1.

13. A process for protecting human hair and skin from the harmful effect of UV radiation which comprises applying the microcapsule according to claim 1 to the skin or the hair.

14. A process for producing the microcapsules of claim 1 comprising the process steps:
a) preparing an oil-in-water emulsion with a disperse phase which comprises the core material and an aqueous continuous phase and the polyvinyl alcohol and
b) subsequently adding the polyoxazoline.

* * * * *